US010527527B2

(12) United States Patent
Budak et al.

(10) Patent No.: US 10,527,527 B2
(45) Date of Patent: Jan. 7, 2020

(54) TISSUE AND CELL STAIN FORMULA WITH A NOVEL MOLECULE OBTAINED FROM PAPAVER RHOEAS

(71) Applicants: Gürer Güven Budak, Ankara (TR); Mehmet Budak, Ankara (TR)

(72) Inventors: Gürer Güven Budak, Ankara (TR); Mehmet Budak, Ankara (TR)

( * ) Notice: Subject to any disclaimer, the term of this patent is extended or adjusted under 35 U.S.C. 154(b) by 224 days.

(21) Appl. No.: 15/520,860

(22) PCT Filed: Nov. 18, 2014

(86) PCT No.: PCT/TR2014/000410
§ 371 (c)(1),
(2) Date: Apr. 21, 2017

(87) PCT Pub. No.: WO2016/064353
PCT Pub. Date: Apr. 28, 2016

(65) Prior Publication Data
US 2017/0315031 A1    Nov. 2, 2017

(30) Foreign Application Priority Data

Oct. 21, 2014 (TR) .................. 2014/12329

(51) Int. Cl.
| G01N 1/30 | (2006.01) |
| A01N 43/80 | (2006.01) |
| C07H 15/26 | (2006.01) |
| C09B 13/06 | (2006.01) |
| C07D 311/30 | (2006.01) |
| A61K 31/7048 | (2006.01) |
| C09B 65/00 | (2006.01) |

(52) U.S. Cl.
CPC ............. G01N 1/30 (2013.01); A01N 43/80 (2013.01); A61K 31/7048 (2013.01); C07D 311/30 (2013.01); C07H 15/26 (2013.01); C09B 13/06 (2013.01); C09B 65/00 (2013.01); *G01N 2001/302* (2013.01)

(58) Field of Classification Search
CPC .. A61K 31/7048; C07D 311/30; C07H 15/26; G01N 1/30; C09B 65/00; A01N 43/80
USPC ............................................. 536/8
See application file for complete search history.

(56) References Cited

U.S. PATENT DOCUMENTS

| 6,159,445 A * | 12/2000 | Klaveness ............ A61K 49/001 424/9.1 |
| 2007/0129282 A1* | 6/2007 | Ahlem ................... A61K 31/56 514/63 |

FOREIGN PATENT DOCUMENTS

WO    WO9505169 A1    2/1995

OTHER PUBLICATIONS

Yadava et al, Fitoterapia, 1998, vol. LXIX, No. 5, 443-444.*
Olennikov et al, Chemistry of Natural Compounds, Jul.-Aug. 2013, 49(4),610-616.*
Gupta et al, Bioorganic Medicinal Chem., 2013, 21, 1116-1122.*
Kostic et al, J. Medicinal Plants Res., 2010, 4(17), 1727-1732.*
Danijela A Kostic et al. "Phenolic contents; antioxidant and antimicrobial activity of *Papaver rhoeas* L. extracts from Southeast Serbia", Journal of Medicinal Plants Research, Sep. 4, 2010, pp. 1727-1732.
Markham et al. "The structures of amentoflavone glycosides isolated from Psilotum nudum", Phytochemistry, Pergamon Press, GB, vol. 23, Aug. 21, 1984, pp. 2053-2056, ISSN: 0031-9422.
Shashank Kumar et al. "Chemistry and Biological Activities of Flavonoids: An Overview", The Scientific World Journal, vol. 4, No. 10, Jan. 1, 2013, pp. 847-16.
Sunday Ewaoche Itodo. "Phytochemical Properties and Staining Ability of Red Onion (*Allium cepa*)Extract on Histological Sections", Journal of Cytology & Histology, vol. 05, No. 06, Jan. 1, 2014.

* cited by examiner

*Primary Examiner* — Ganapathy Krishnan
(74) *Attorney, Agent, or Firm* — Gokalp Bayramoglu

(57) ABSTRACT

A *papaver* from *rhoeas*' cell and tissue stain is formulated incorporating a new one bioflavonoid which specifically stains the nucleus for microscopic evaluation in histopathology, microbiology and cytology. It appears to be an alternative to hematoxylin for routine usage. Biochemical name of this compound is hydroxy-7-methoxy-2-(4-methoxy-3-(((2R,3R,4S,5S,6R)-3.4.5-trihydroxy-6-((((2R,3R,4R,5R, 6S)-3.4.5-trihydroxy-6-methyltetrahydro-2H-pyran-2-yl) oxy)methyl)tetrahydro-2H-pyran-2- yl)oxy)phenyl)-4H-chromen-4-one. NMR analysis shows the biochemical structure of molecule is a bioflavonoid. (FIG. 4,5) Molecule within *Papaver rhoeas* along with the synergistic and other molecules penetrates the biologic and nonbiologic samples. Combining with the other synergistic mechanisms the stain formula is prepared. The amount and type of Mordant and pH are the parameters that affect the quality and timing of the staining results.

17 Claims, 18 Drawing Sheets

Figure 1: Techniques used for developing the Papaver rhoeas formula

Figure 2: Papaver rhoeas Formula Precursor Preparation

Figure 3: Papaver rhoeas Stain Formula Precursor

Figure 4: Papaver rhoeas molecule —cis —trans configuration

X=N,O,S,C
R=H,OH,NH2,Cl,Br,I,F,O-CH3,(any aliphatic complex)

Figure 5: Papaver rhoeas molecule's name and configuration

5-hydroxy-7-methoxy-2-(4-methoxy-3-(((2R,3R,4S,5S,6R)-3,4,5-trihydroxy-6-(((2R,3R,4R,5R,6S)-3,4,5-trihydroxy-6-methyltetrahydro-2H-pyran-2-yl)oxy)methyl)tetrahydro-2H-pyran-2-yl)oxy)phenyl)-4H-chromen-4-one Chemical Formula: $C_{29}H_{34}O_{15}$
Exact Mass: 622.18977
Molecular Weight: 622.57126
m/z: 622.18977 (100.0%), 623.19313 (31.4%), 624.19648 (4.7%), 624.19402 (3.1%)
Elemental Analysis: C, 55.95; H, 5.50; O, 38.55

Figure 6: Grades of Papaver rhoeas Stain Formula

Figure 7: Papaver rhoeas Fomula Stain Methodology

Figure 8: PAPAVER rhoeas Fomula Differentiation

Figure 9: Staining Pattern of the Papaver Rhoeas Formula

Figure 10: Cell-Tissue Stain Example of Papaver rhoeas Formula

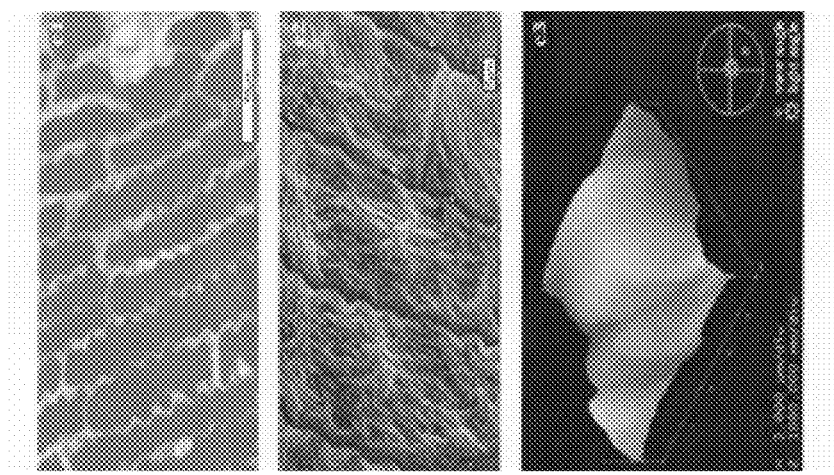
Figure 17: Atomic Force Microscopy
Cisternal structures within Petals filled with aqueous content

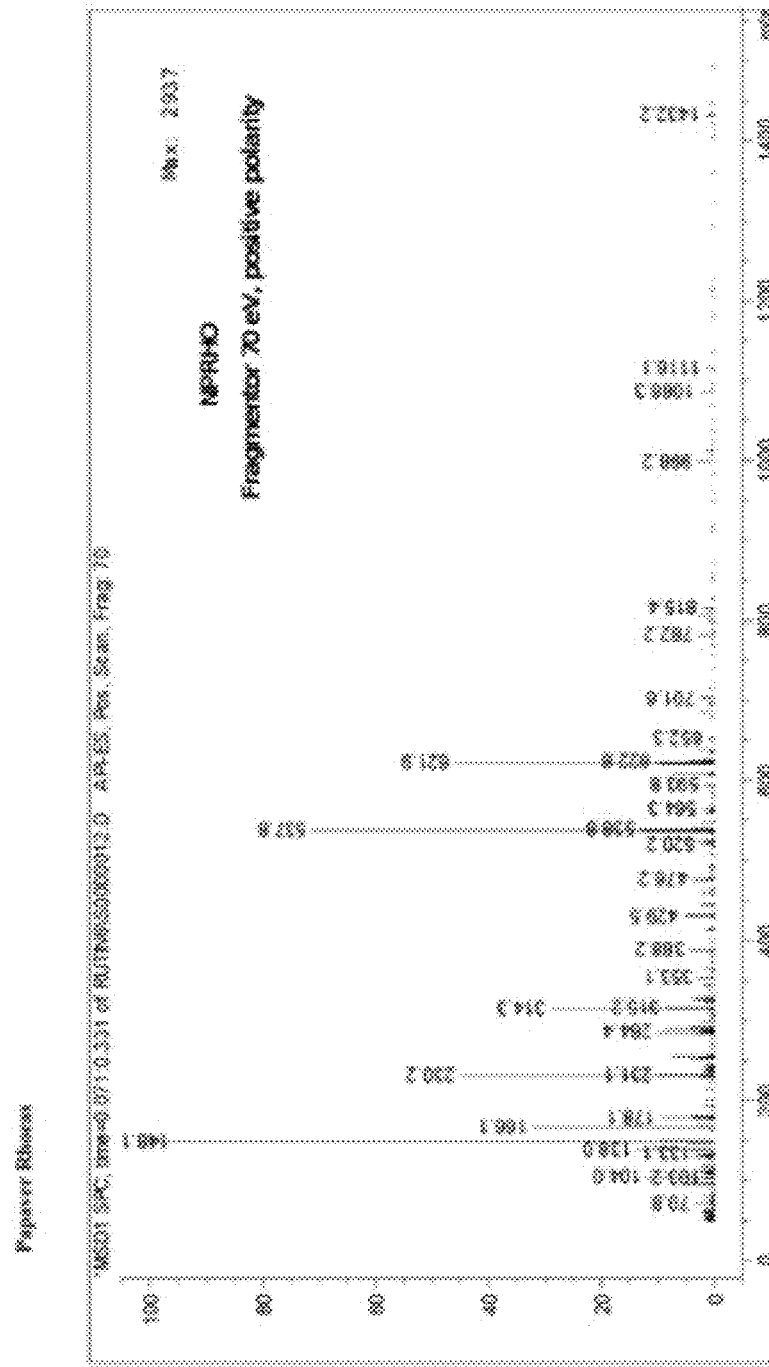
Figure 18: NMR results

TISSUE AND CELL STAIN FORMULA WITH A NOVEL MOLECULE OBTAINED FROM PAPAVER RHOEAS

CROSS REFERENCE TO RELATED APPLICATIONS

This application is the national phase entry of International Application No. PCT/TR2014/000410, filed on Nov. 18, 2014, which is based upon and claims priority to Turkish Patent Application No. 2014/12329, filed on Oct. 21, 2014, the entire contents of which are incorporated herein by reference.

TECHNICAL FIELD

*Papaver rhoeas* stain contains, a new bioflavonoid along with the derivatives and synergistic molecules. New nuclear stain is formulated from *Papaver Rhoeas* extract for diagnostic purposes providing a specific staining for the nucleus of the 'cells and tissues'. The current invention is related to a stain which is an alternative formulation of the routine stain of "hematoxylin" as well as having the benefits for diagnosis in health sector and contribution to the economy.

Overview

*Papaver rhoeas* formula is mainly used as a nuclear stain and it contains a new molecule and may contribute 10-15 billion dollars to the economy yearly and which is an alternative to hematoxylin. The source will contribute efforts for preserving the world's endangered rainforests balancing the regional ecological systems and would be useful as an industrial product.

*Papaver rhoeas* formula is a rational alternative to conventional stain of Hematoxylin which is used in routine diagnostics. Increasing need for Hematoxylin is due to increasing the number of human population and the diagnostic therapeutic medical procedures. The sale price for hematoxylin for per gram is very high and the production is risking the world rainforests as well as imposing a risk to the ecological system.

*Papaver rhoeas* herein is a new cell-tissue dye source which has been discovered and formulated. Papavera *rhoeas* molecule is in very active, functional which is a bioflavonoid molecule and combined with eosin. Molecule itself and along with derivatives and synergistic molecules provide a clear staining in the nucleus in the tissue and in other sources such as fungi from microbiological samples allowing the fine staining details, and can be applied to histopathology, cytology for diagnostic purposes. A broad spectrum of colors and illuminating and detailing the features in diagnostics providing new diagnostic parameters and the findings.

The methodology for staining in hospitals, laboratories and manufacturing, donanım equipment and materials are the similar to traditional techniques without significant additional investments. The molecule can be used as the immune system regulator, T-cell activator, anti-viral agents, tissue protective and regenerating as well as and Indicator and for the synthesis of new vitamin complexes. It can be also use as dye in the wine industry still inert dye in order to color the food, military uniforms, especially for baby clothes and toys and again in eco-friendly textile as a coloring agent, and as skin rejuvenating and smoothing and can be used as a spot treatment and anti-wrinkle agent. Cosmetics products are used in the dyeing of surgical prostheses and surgical sutures. Find applications for biochemical diagnostic tests. Especially in industrial plasma tv, monitor screen and nanotechnology for the production and sensor technology for nanoparticle synthesis and also can be used to produce printer cartridges, letting the paint. Again, immunohistochemistry or in combination with other digital image technology will be used for diagnostic purposes.

BACKGROUND OF THE INVENTION

*Papaver rhoeas* is a naturally growing in nature. The name species name is *Papaver rhoeas* L, scientific pedigree name is Papaveraceae. Other names are red Poppy, Corn Poppy, Flanders Poppy, Shirley Poppy *Papaver Papaver Papaver Roubini Papaver tenuissima Papaver tumigil Papaver trilobum Papaver strigosum* there are the same species (1-6). There is usually a black spot on the petal of various sizes 2 and 4 big hairy sepals and has red leaves. Ovarian is located in the center and is surrounded by a black field. The amount of pollen varies depending on the fruit size, contains more than 200 seeds per fruit.

*Papaver rhoeas* grows in sunny climates and grows best in sandy soils. Petal of Papavera *Rhoeas* has chemically occurring color and gives the reaction involving the Papaveric acid. It has soothing effect emollient, and menarche regulating, expectorant, hypnotic, moves slightly narcotic and sedative properties (7-9). are useful in the treatment of fever, bronchitis symptoms and cough, insomnia, digestive disorders and for the the pain. (10-12). Also it can be used for nervous system symptoms such as hyperactivity and insomnia. It is also shown to safe for children (13-15).

Flavonoids have phenolic structures which is naturally present in fruits, vegetables, grains, bark, roots, and again found in flowers, tea, and wine (16). more than 5000 varieties of flavonoids has been detected however the specific effect is shown very rarely. Bioflavonoids flowers are responsible for the color of the fruit (17-20). Intake with food lower the cardiovascular disease and reduced the mortality rate. (21,22) The derivatives are also seen in vegetables and still shows its characteristics as vitamins, such as vitamin P (routine), as an example. (23) Vascular permeability of the capillary wall (24) is increased by flavonoids which was discovered in the 1950s. Flavonoids are divided into 4 main groups (25,26) on and (27) can be divided into subgroups. Flavonoids have been shown for each group of characteristic in molecular structure.

Flavone has a double bond on the aromatic ring in the center, has a planar structure. Flavonoids include 2-Phenyl Benzopiren aromatic heterocyclic ring. Bioflavonoids give color to the plant, also plays an important role in flavonoids plant growth and development. Creating a natural barrier against UV-B rays with mushrooms bioflavonoids helps prevent opportunistic fungus growth. Antimicrobial and antiparasitic effects are shown. Genetic changes made to microorganisms flavonoid molecules with microorganisms can produced. But technically these are expensive methods. (28)

According to the IUPAC 4.5 the flavonoids are divided into 2 groups as isoflavonoids and neoflavonoids. These are 3-phenyl chromen-4-one (3-phenyl-1,4-benzopyran) derived from the structure isoflavones and phenylcoumaran the (4-phenyl-1,2-benzopyran) derived from the structure of bioflavonoid.

Bioflavonoids are given the name the compound depending on whether containing a ketone and their flavones and flavonols. Flavonoids term also loosely than in a non-polyhydroxy ketone is used to describe the compounds of the polyphenols. Flavonoids has three rings or heterocyclic structure has the configuration shows the overall 3-ring structure phloroglucinol model. Isoflavonoid molecules can be produced by genetic engineering. (28)

*Papaver rhoeas*, petals and capsules produces some alkaloids. These alkaloids do when heated with acid is converted to an active complex called the Porphyrin. Result of an unknown reaction complex alkaloids, take a red color. In Klayman regarding "red coloring principle" is called. (29-33) and color develops in relation to pH of reactions. (33-35)

Bioflavonoids control the oxygen damage by preventing lipid peroxidation (36-38) accelerating the reactions as an antioxidant against reactive oxygen radicals. (39,40) through superoxide dismutase, catalase, and glutathione peroxidase, ascorbic acid, and α-tocopherol such as reducing agents reduce the internal oxidation reactive oxygen species (41).

Some flavonoids converts the reactive oxygen-derivatives to inactivated radical peroxynitrite (42). Many flavonoids may interact the endothelial cells and macrophage in which decreases nitric oxide, nitric-oxide synthase activity (43) and thus react with extremely harmful peroxynitrite induces production of oxygen free radicals.

Flavonoids effect as an antioxidant, it is also due to eliminate residual free radicals and therefore cause less damage and can also react with nitric oxide (44) and Nitric oxide molecules, (45) is inhibited by flavonoids Flavonoids oxidative damage (46,47), resulting in inhibiting the oxidase activity of xanthine (48) and allows reduction in leukocytes inflammation (49) Some flavonoids superoxide production (50) inhibit degranulation of neutrophils without any effect. Mast cell degranulation is directed within membrane s Ca2+receptor has an effect on the control of the channel. (51,52)

Flavonoids have an iron-binding and iron-stabilizing properties also inhibits the lipid peroxidation. (53-56) inhibit. Some flavonoids (57-59) reduce the inflammatory cells as neutrophils adhesion gives an optimum inflammatory reaction. However, in general, can reduce complement activation. Flavonoids reduces peroxidase emissions. Al-antitrypsin activation by this reduction, inhibits the production of reactive oxygen radicals. Proteolytic enzymes will show progressive inactivation of arachidonic acid on the enzyme systems (60-62) along with the anti-inflammatory and anti-thrombogenic properties are given (63).

Studies of the average daily intake of flavonoids are limited. For instance, the consumption of vitamin C is more than three times the intake of flavonoids (64) Flavonoid consumption varies greatly among countries (65,66). Determining food intake of flavonoids with the cohort studies are difficult. Studies related to the metabolism Absorption and excretion of flavonoids in humans are limited too. (67-72) Glycosylated form is absorbed greater than the aglycone form. The conjugation takes place in the bowels and in liver. (73)

The metabolism of flavonoids begins in the intestinal cells, a glucuronide of conjugation is formed by binding the albumin after transported to the liver and a sulfate group, adding a methyl group, or both of conjugation of flavonoid is completed. Higher Active conjugated bioflavonoid the lower the rates of mortality and cardiovascular disease in the Mediterranean.

The so-called toxic effects of bioflavonoids are not well well studied. (74-79) There are many discussions about the even mutagenic properties. (80-82) However, other studies in humans over long work shows that the low probability of definite carcinogenic side effects. Flavonoids are toxic to cancer cells or immortalized cells, but these are molecules is less toxic to normal cells. (83-85) of flavonoids, in vitro studies, antiallergic agent, antioxidant, anti-microbial, anti-bacterial, anti-fungal, like some other biological and pharmacological activity has been shown to have anti-viral effect.

Antiviral activity of flavonoids, Wang et al (87) was shown in a study conducted by Herpes simplex virus HIV as well as respiratory syncytial virus, parainfluenza virus, and adenovirus The effects of flavonoids may differ for the different stages in the replication cycle of the virus (88). Form of the flavonoid aglycone (89) has an effect on rotavirus inhibitory. Anti-HIV agents as reverse transcriptase or DNA-directed RNA polymerase (90) there are studies on the inhibitory activity. A significant contribution to the treatment of previously defined flavonoids for treating patients infected with HIV make benefits is not certain. (91) In vitro studies in flavonoids leukemia (MLL) gene is believed to be important in the development of DNA replication mutation effects by inhibiting topoisomerase enzymes. Cyclooxygenase and lipoxygenase seen through anti-inflammatory effects. Membrane tyrosine kinase (92, 93) is the nature of inhibiting various immunological responses flavonoids.

Endothelial angiogenesis is regulated by a number of developing reaction. With flavonoid intake has an inverse correlation between lung cancer and melanoma growth rate. However, the mechanism is not clear at the back of flavonoids anti angiogenic effect. A possible mechanism of protein kinase (94-104) may be the inhibition.

Clinical studies in men did flavonoid taken regularly consumed foods and appears to reduce the risk of death from coronary heart disease. In addition, dementia (105,106) is proposed to prevent the development of flavonoid intake. Total plasma cholesterol concentrations inverse correlation between the presence of oxidative stress and vascular damage has been reported. Intake of flavonoids reduces the risk of dementia. Altering vascular inflammatory mechanisms, arterial blood pressure and hypertension are highly regulated. Blood vessels inhibits oxidative stress related signaling pathways in cells and by increasing capillary endothelial function, reducing the risk of atherosclerosis. Thrombus formation is inhibiting clot formation by inhibiting platelet aggregation. Flavonoids have (a) a direct antibacterial activity, (b) synergistically with antibiotics with activity, and (c) to have same effects suppressing bacterial virulence factor.

Moreover, inadequate procedures and limited working with oxidative cell damage and objective to measure the in vivo measurement of the effects of extreme amount of force. Develop analytical techniques to ensure the collection of more data on the absorption and excretion are required. Under the light of today's information, flavonoid intake is recommended (107-112) fruits, vegetables and beverages (eg, tea and red wine.

In Histopathology and cytology for the diagnosis, teaching and research purposes, the fixed and live tissue and cell samples are stained to identify specific pathological features with microscopic examination and evaluation to determine the diagnostic features in the tissue and the cells. First a glass slide for tissue or cell samples for microscopic evaluation is placed. These samples before staining with *Papaver rhoeas* formula, are colorless, semi-transparent or transparent. The new formula penetrates tissue layers aggressively and reaches the cell membrane and then the nucleus. The stain provided by the formulation of the content is the coloring method and appropriate microscopic assessment is provided and to understand the features showing the relationship between the required information about structures and must ensure a proper necessary coloring to distinguish the structures again in tissue and cells.

BRIEF DESCRIPTION OF THE DRAWINGS

FIG. 17: Atomic force microscopy reveals cisternal structures within *Papaver rhoeas* petals FIG. 18: NMR analysis of *Papaver rhoeas* molecule

TERMS AND DEFINITIONS

Figure 1:
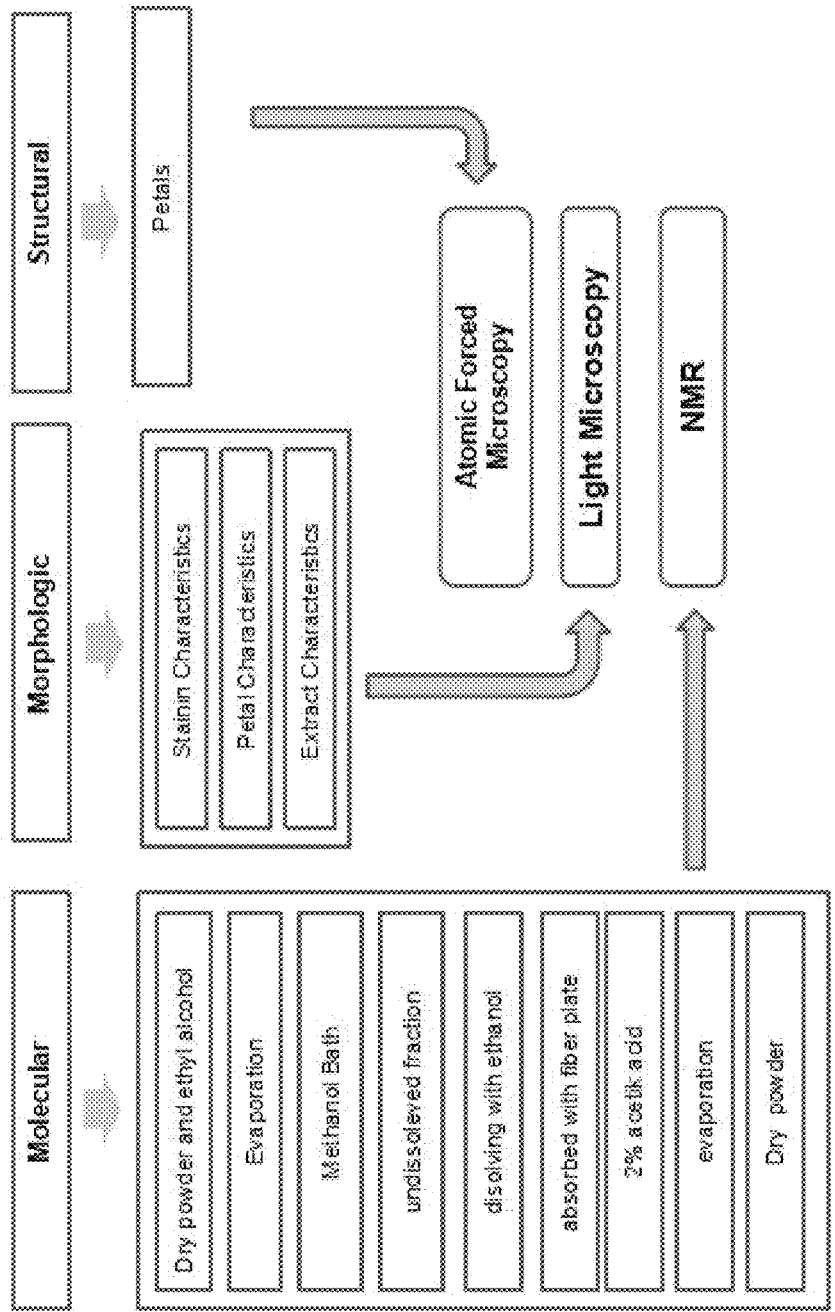
FIG. 1: *Papaver rhoeas* Tissues and Cells Stain formulation analysis methods

I. this invention is related to a stain of the nuclei of the cells in biological samples is described a new cell tissue dye (*Papaver rhoeas* Cell Texture Paint). This painting has been discovered that contain a new active bioflavonoids.

II. Terms are used to describe the present invention better for the practice and to explain it conveniently.

III. If there are any new specific terminology, the properties of the new term is explain, and is described in elaborating the details IV. Definitions can be expressed as single or plural. Values are not limited to the exemplified values.

V. "derivative" is addressed in terms of number of molecules having 1, 2, 3 may be, and this number may be reduced to 4 or less or to increase it to specific embodiments.

VI. "synergistic molecule" in address to meaning of the number of molecules having 1, 2, 3, and this number may be increased to 4 or more, and for those specific purposes of the invention.

VII. Typically, tap water as a rinse solvent in the staining protocols are used very economical. Indeed As used herein, "water", the term includes applications such as distilled or deionized water is used as well as the tap water, specified.

VIII. "biological sample" is a prokaryotic origin, kokel archaeal or eukaryotic origin (for example, insects, protozoa, birds, fish, reptiles). Or mammalian (e.g., rat, mouse, cow, dog, donkey, guinea pig or rabbit) or primate (e.g., example, chimpanzee or human) can. Can be obtained in vivo or in vitro biological tissues or fluids. Such samples, body fluids (such as blood, blood plasma, serum or urine), including, cells, cell organelles, isolated organs, biological specimen Although tissues and fractions may contain all or part of it. Biological samples are also extracted from a part of biological sample. Biological samples protein may comprise carbohydrates and nucleic acids.

IX. Cytological for biological samples, tissues and biological fluids and not limited to the sampling are to evaluate the invention. Body cavities washes, eye wash fluid, skin barrier, cheek salivary glands, blood and the vaginal glands, bone marrow, urine, preejakulat nipple aspiration, semen, milk, sputum, mucus, pleural effusion, pelvic fluid, synovial fluid, ascites fluid, pap smear, rectal swab, aspiration, needle biopsy, surgical or autopsy fluids, tissue specimens, plasma, serum, spinal fluid, lymph fluid, sweat, tears, sputum, saliva, tumors, fluids, organs and in vitro cell lines and tissue cultures that cytological sampling one. Biological cell and tissue samples may be used in dyeing process after fixing as embedded in paraffin. This preparation is placed on the document glass for investigation. Samples can used for coloring the fungi, parasites and microorganisms. Technical difference of the preparation for the dyeing step of the biological sample does not represent any limitation to the invention.

X. Dye solution is stored at room temperature using a liquid such as water or chemical solvents, in a solvent. Water (approximately 50% and more by volume) and contains liquid or polyols comprising one or more lower alkanols and water. Varies according to modifications. The solvents to be used are ethanol, distilled water, methanol, running water, ethylene glycol, propylene glycol, methanol and formaldehyde can be mentioned.

XI. The term describes the antioxidant capacity of molecules with a higher oxide and the molecule is in the same environment that prevents oxidation of other molecules.

XII. The lower alkanol molecule; OH group, alkyl group (a methyl group, ethyl group, n-containing is an alkyl group of 1-5 carbon atoms)-propyl group, (isopropyl group, n-butyl group, a butyl group, a t-butyl group, n-group, isopentyl group, neopentyl group, or pentyl.) and low (alkanols are methanol, ethanol and isopropanol) may be added.

XIII. The term refers to the secondary oxidant molecules having a stronger reduction potential than other molecular. Different chemical oxidants may be used for different formulations. Iodine salts and potassium iodate, sodium iodate, zinc oxide, permanganate salt or potassium permanganate, sodium periodate, potassium periodate salts and peroxides, hydrogen peroxide, periodate, calcium hypochlorite, kloramit, lime chloride, sodium iodate, zinc oxide, iodine, sodium hypochlorite, oxidation example hydrochloride, and barium hydroxide.

XIV. Mordant can bind a cationic complexing of the dye molecules which are metals. New molecules can detect DNA within cells, myelin, elastin and collagen fibers of muscle striae and mitochondria, are also connected to the synergistic effect of the molecule. Mordant examples can be listed as follows in, aluminum sulfate, aluminum potassium sulfate, aluminum ammonium sulfate, aluminum chloride, iron, tungsten, zirconium, bismuth, molybdenum fosfomolibic acid or molybdic acid, vanadium (vanadate) aluminum or ammonium alum, aluminum sulfate, potassium alum, aluminum acetate, calcium chloride, aluminum nitrate, iron, ammonium sulfate, ferrous sulfate, potassium ferrocyanide, potassium ferricyanide, ferric chloride, copper acetate, iron alum, aluminum, bismuth nitrate, molybdenum acid and phosphomolybdic acid. Mordant different metals will create different colored fractions. for instance; Aluminium purple-blue, iron; blue-black, chrome; Blue-black, copper; Blue-green, Nickel; purple, Tin; red, Lead; dark brown; Osmium green brown XV. Stain formula mixture is prepared by adding acid to the cells of the biological sample is increased by the nucleus staining specificity. For this purpose acetic acid, salicylic acid, citric acid, hydrochloric acid, sulfuric acid, saturated ethanolic formic acid may be used ascorbic acid.

XVI. The term antioxidants is used in the sense stabilization which helps to keep the optimum duration of the dye oxidation and extends shelf life. The stabilizer glycerol, chloral hydrate, diethylene glycol, potassium iodide, ethyl glycol request.

XVII. "molecule" is an organic molecule may be linked through various points of attachment to other molecules and form complex structures. The new composition and molecular structure can be specifically created diversity with the molecules of dye combinations composition. different molecular structures and synthesized structures attached to these molecules and different properties can form derivatives showing. Some examples of these polysaccharides means. Amylose or cyclodextrin and many aldose ring, monosaccharides, glucose, fructose, and galactose, disaccharides (sucrose), other binding molecules still crypts ethers such as maltose and lactose, dendrimers, nanotubes, kalisaneres, valinomyc and nigericin considered.

XVIII. Throughout the specification of disclosing the invention and claims, the term are used in the specific language expressions. the term "about" means the specified value is not limited to the exact value modified by a term. Unless otherwise stated, such like used herein molecular weight, reaction conditions and ingredients, such as in the claims, all numbers expressing quantities of features, it should be understood that in each case be modified by the term. Accordingly, unless indicated to the contrary may be detailed in the following description wherein at least the number of significant digits for each numerical parameter specified by the desired properties and its numerical parameters set forth light.

XIX. The term of "alkyl" means a branched, straight chain alkyl groups (for example, methyl, ethyl, propyl, butyl, pentyl, hexyl, heptyl, octyl, nonyl, decyl, etc.) refers to a saturated aliphatic groups, including. Chain alkyl groups (isopropyl, tert-butyl, isobutyl, etc.) A straight chain or in branched chain alkyl backbone to arm 6 or with fewer carbon atoms (e.g., C1-C6, for C3-C6 branched chain, straight chain), spinal cord (e.g., C1 to C4 straight chain or 4 or fewer carbon atoms, for C3-C4 branched chain). "C1-C6" alkyl refers to alkyl groups containing 1-6 carbon atoms. As used herein, the term "C1-C4" alkyl means alkyl groups containing 1-4 carbon atoms. Moreover, the term alkyl, both "unsubstituted alkyls" and including "substituted alkyls" of the latter half of the substituted hydrocarbon backbone means alkyl having substituents replacing a hydrogen on one or more carbons. Such substituents include, for example, (C1-C4) alkyl, (C1-C4) alkoxy, amino, ((C1-C4) including alkylamino, and (C1-C4) dialkylamino), cycloalkyl and (phenyl, including naphthyl to) aryls, hydroxyl, cyano, halogen, or nitro. Aryl Alkyl and cycloalkyl substituents also shown as described above.

XX. The term of "alkoxy" refers to an oxygen atom covalently linked substituted and unsubstituted alkyl, alkenyl and alkynyl groups means. Examples of alkoxy groups include methoxy, ethoxy, isopropoxy, propoxy, butoxy, pentoxy, but is not limited thereto. In some embodiments, has a straight chain or branched chain alkoxy of four or less carbon atoms, branched skeleton (for example, C1-C4 straight chain, C3-C4 branched chain). As used herein, "C1-C4" alkyl refers to alkyl groups containing 1-4 carbon atoms.

XXI. As used herein, "amine" or "amino" means the structure in which at least one carbon or changed or a nitrogen atom is covalently bonded to the heteroatom. Alkyl groups can be in the backbone of 4 or having fewer carbon atoms (for example, C1-C4 straight chain, C3-C4 branched chain), (C1-C4) alkylamino, nitrogen is at least one additional C1-C4 bonded to an alkyl group means that groups and compounds. "(C1-C4) alkylamino, the nitrogen is bound to at least two additional C 1-C 4 alkyl group refers to groups and compounds.

XXII. The term of, "aryl" includes, for example, benzene, phenyl, pyrrole, furan, thiophene, groups containing thiazole zero to four heteroatoms, for example, refers to 5 and 6-membered single-ring aromatic groups, isothiazole, imidazole, triazole, tetrazole, pyrazole, oxazole, isoxazole, pyridine, pyrazine, pyridazine and pyrimidine, and the like. In addition, "aryl" refers to multicyclic aryl groups, e.g., tricyclic, bicyclic, e.g., naphthalene, benzoxazole, benzobisoxazole, benzothiazole, benzimidazole, benzothiophene, methylenedioxyphenyl, quinoline, isoquinoline, such groups also include indole, benzofuran, purine, benzofuran, includes deazapurine structure or with heteroatoms in indolizine.halk these aryl groups, "aryl heterocyclic", "heteroaryl" or "heteroaromatic can also be expressed as follows." An aromatic ring as described above, such as is found in one or more ring positions with such substituents, (C1-C4) alkyl, (C1-C4) alkoxy, ((C1-C4) alkylamino and (C1-C4) including dialkylamino) amino, hydroxy, cyano, halogen, or nitro. Aryl groups can also be fused, a polycycle (e.g., tetralin) creates enough non-aromatic alicyclic or köprülenebilir.heteroaril includes, for example Lazarus heterocyclic rings include oxirane, dithiet to, pyrroline, pyrrole, furan, dihydrofuran, dihydrothiophene, thiophene, pyrazole, imidazole, oxazole, thiazole, isothiazole, 12,2,3-triazole, 1,2,4 includes unsaturated cyclic compounds, triazole, dithiazole to, tetrazole, pyridine, pyran, pyrimidine, pyran, thiapyr valve, diazine, thiazine, dioxin, triazine and tetracene.

XXIII. The term of "antibody" specifically binds to a particular spatial and polar, so that a further refers to an immunoglobulin molecule defined as complementary to the organization. The antibody may be monoclonal or polyclonal and either continuous hybrid cell of the collection of the secreted protein (monoclonal) or formed by the collection of host serum (polyclonal) is obtained. Antibodies are complete immunoglobulin, or may comprise a fragment thereof, e.g., IgA, IgD, IgE, IgG1, IgG2a, IgG2b and IgG3, ıgm. ç e ş itl classes and isotypes, functional antibody fragments including, may comprise a portion capable of retaining binding at similar affinity to full-length (for example, Fab, Fv and F (ab'). Sub.2 or Fab').

XXIV. The term of binder; refers to a molecule capable of binding one or more targets in the biological sample. The binders can be connected in a unique way to a destination. Suitable binders include natural or modified peptides, proteins (e.g., antibodies, they afibo or aptamers), nucleic acids (e.g., polynucleotides, DNA, RNA, or aptamers) may include; polysaccharides (e.g., lectins, sugars), lipids, enzymes, enzyme substrates or inhibitors, ligands, receptors, antigens, or haptens. A suitable binder for the sample to be analyzed which can be selected and determined depending on the current target.

XXV. A suitable binder, for the sample to be analyzed can be selected and determined depending on the current target. For example, a target may include a ligand in the sample and the binder may include a receptor or a target may include a receptor and the binder may include a ligand. Similarly, a target may include an antigen and an antibody or binding fragment thereof, or vice versa, or may comprise antibodies. In some embodiments, a target may include a nucleic acid and the binder may include a complementary nucleic acid. In some embodiments, both the target and the binder may include proteins capable of binding to each other XXVI. Any change on the new functionality and molecular oven products would not limit the present invention and are considered the possible capacity of the present invention.

DETAILED DESCRIPTION OF THE INVENTION

Figure 11:
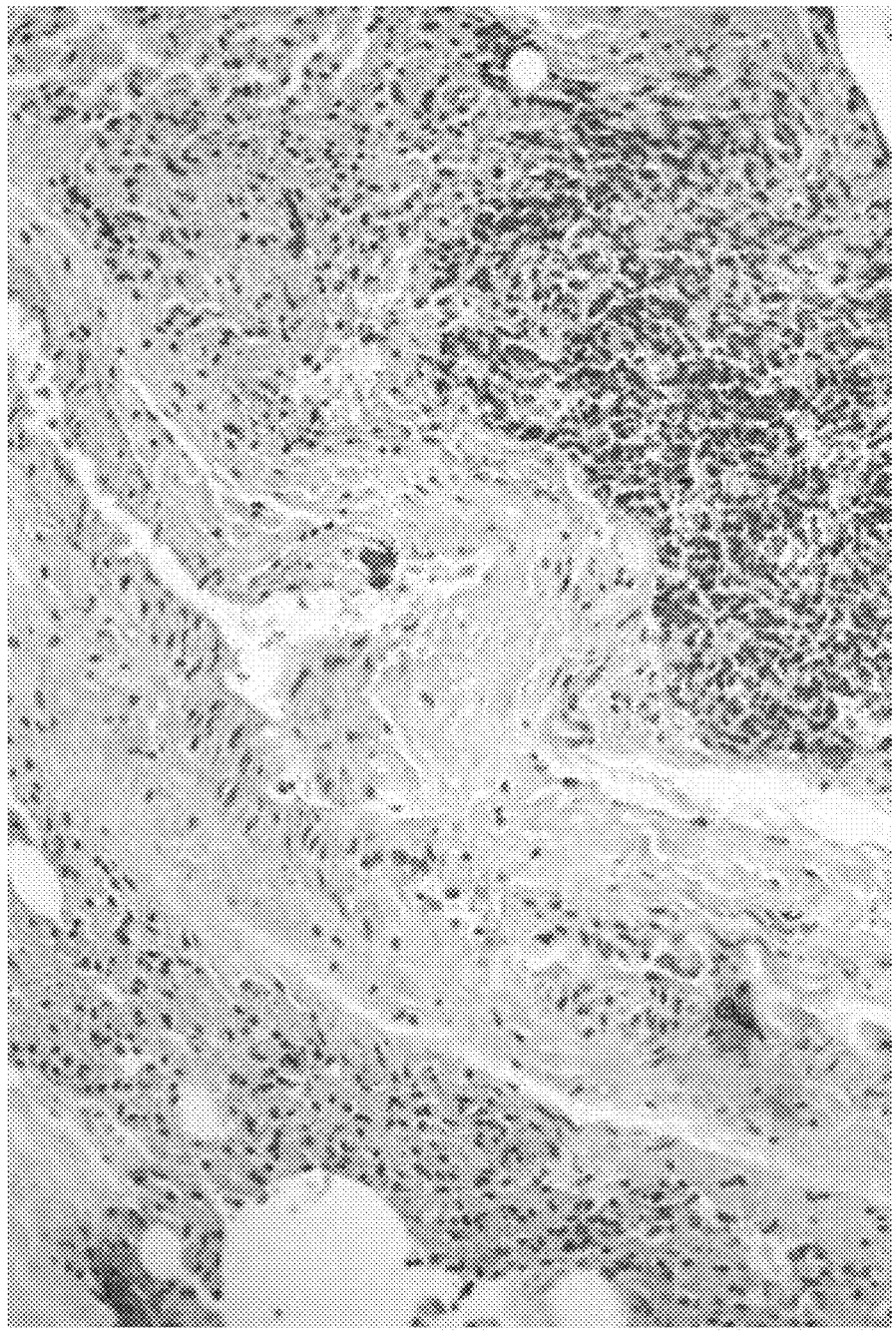
FIG. 11: *Papaver rhoeas* Formula highlights the specifically the cell nuclei in lung tissue
Figure 12:
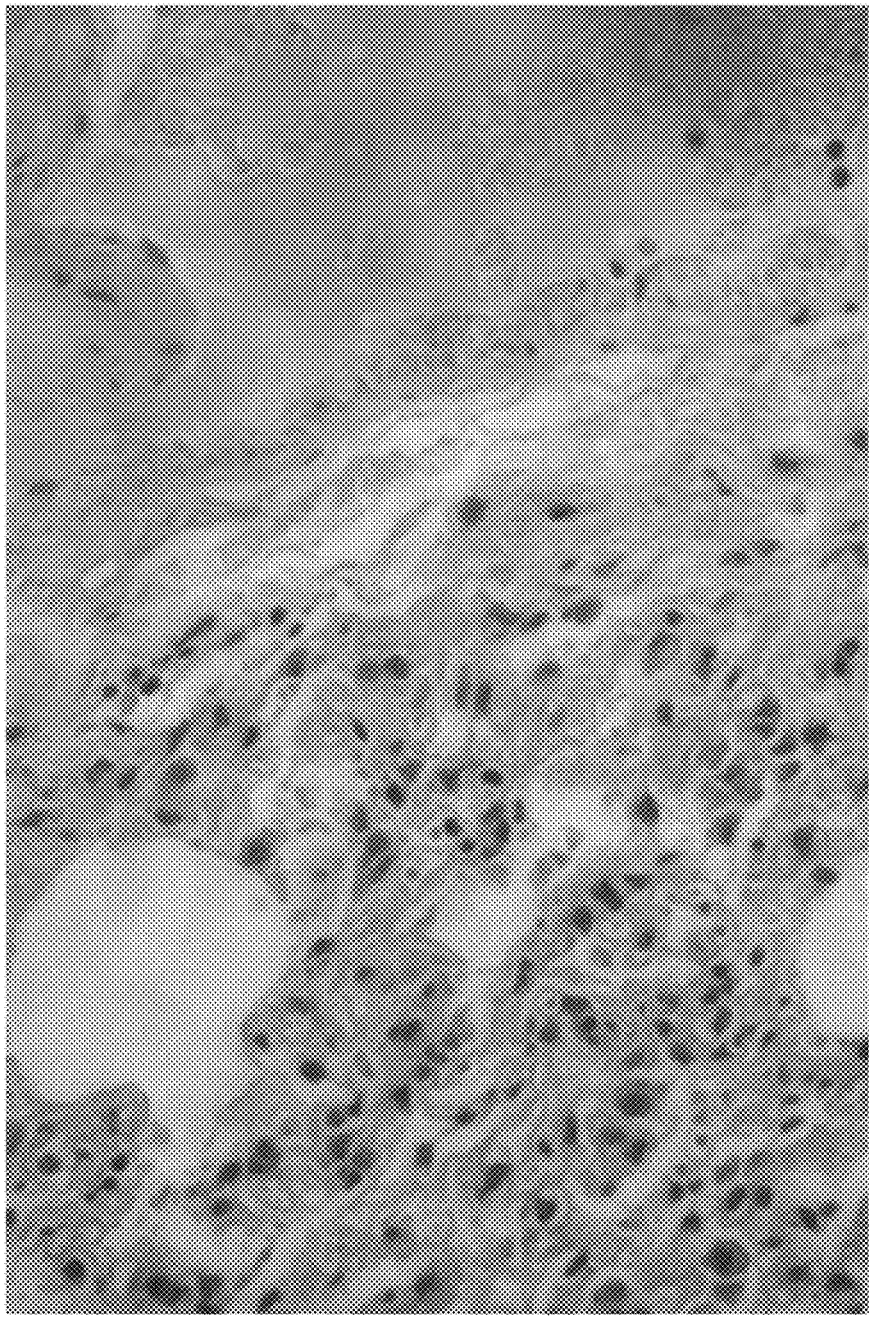
FIG. 12: *Papaver rhoeas* Formula highlights the specifically the cell nuclei in lung tissue

New cell nuclear stain obtained from *Papaver rhoeas* extract is described in this invention. This new histology paint contains a bioflavonoid very active and functional. *Papaver rhoeas* formula is showing the characteristics of cells and tissue samples as a new nuclear staining demonstrating the biological characteristics of the distinctive patterns applying in histopathology, cytology and microbiology. (FIG. 11,12)

Cell nucleus features are evaluated for the purpose of diagnosis by pathologists and in particular detection of malignant or metastatic cells, however, the separation from diagnosis to help the pathological findings of the normal findings, especially in postoperative surgical specimens and biopsies, fine needle biopsy, smears, washes, and also with invasive or non-invasive method samples and will be used to examine the autopsy preparations.

*Papaver Rhoeas* grows spontaneously in nature, and easily producible to maintain the stain to produce the tissue cell nucleus formula. Stain formula consist a molecule to highlights the nucleus of the nuclei of the cell. The molecules is analyzed and proceeded to other laboratory studies which is presented and illustrated.

Figure 13:
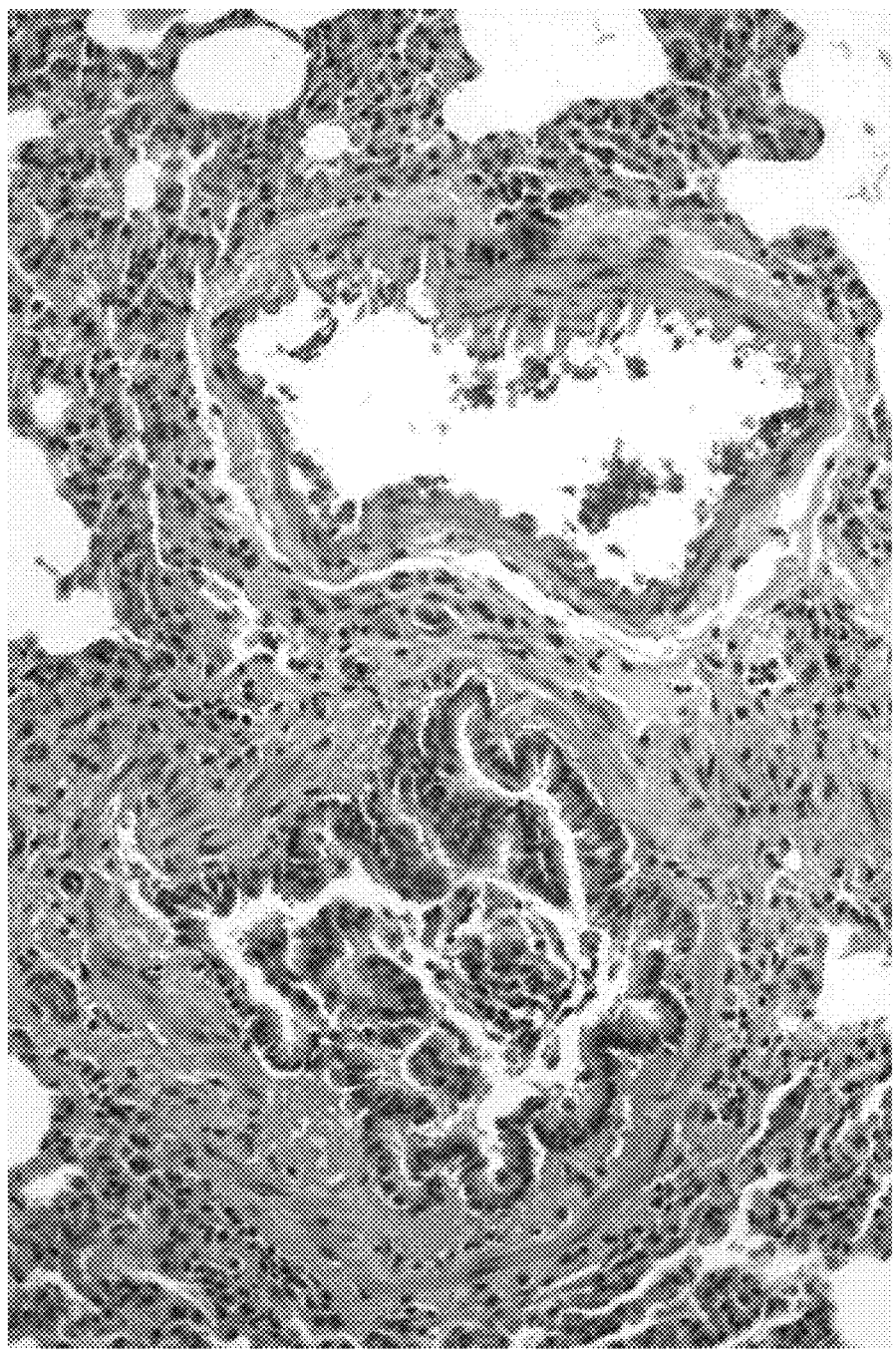
FIG. 13: *Papaver rhoeas* formula with Eosin in lung tissue revealing the nucleus and tissue details

Mordant (metal) is incorporated to provide sufficient and stable staining and the acid is added. *Papaver rhoeas* formula showed the permanent staining properties with the clear cell morphology and in concise manner. Especially when it is combined with eosin stain, *Papaver rhoeas* formula stains the tissues and cells, tissue layers, membranes, muscle tissue, intranuclear or intracytoplasmic structures and are colored with fine details. (FIG. 13,14)

The extended length of the storage time on the dye solution is oxidized naturally or chemically. (113.114) Optimum efficiency and amount of use of an oxidative agent will prevent the formation of the product from over-oxidization (115,116)

The fluctuations in the dye concentration interferes the stability of the staining (117). This time should be replaced with the application of the stain must be corrected. The intensity of the stain is evaluated visually. A trained expert evaluate the staining and adjust the intensity of staining until reaching the desirable staining quality.

Flavonoids contain two aromatic rings in general. Each of these ring forms at least one hydroxyl group and 6-heterocyclic ring design with three-carbon bridge. Flavonoids subgroups are formed due to the heterocyclic ring to a bonded aromatic ring depending on the oxidation state of the characteristics or function groups and heterocyclic structure and the bound fraction.

This molecule using binders to connect to different groups and atoms which are natural or modified peptides, proteins (e.g., antibodies, or aptamers), nucleic acids (e.g., polynucleotides, DNA, RNA, or aptamers) polysaccharides (e.g., lectins, sugars), lipids, enzymes, enzyme substrates or inhibitors, ligands, receptors, antigens or haptens. Similarly, connected target group may be an antigen and an antibody or antibody fragment. *Papaver rhoeas* in this formula targets the nucleic acid.

Figure 2:
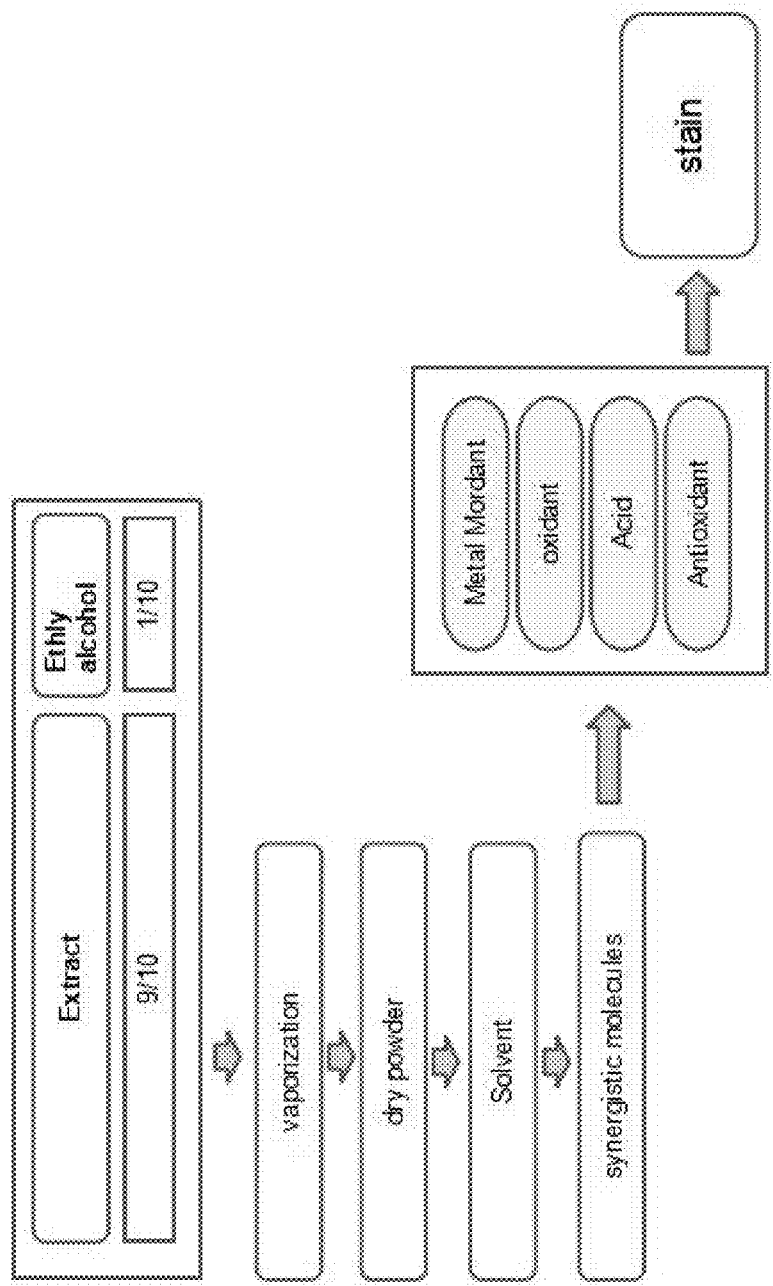
FIG. 2: Preparation Phases for *Papaver rhoeas* formula
Figure 3:
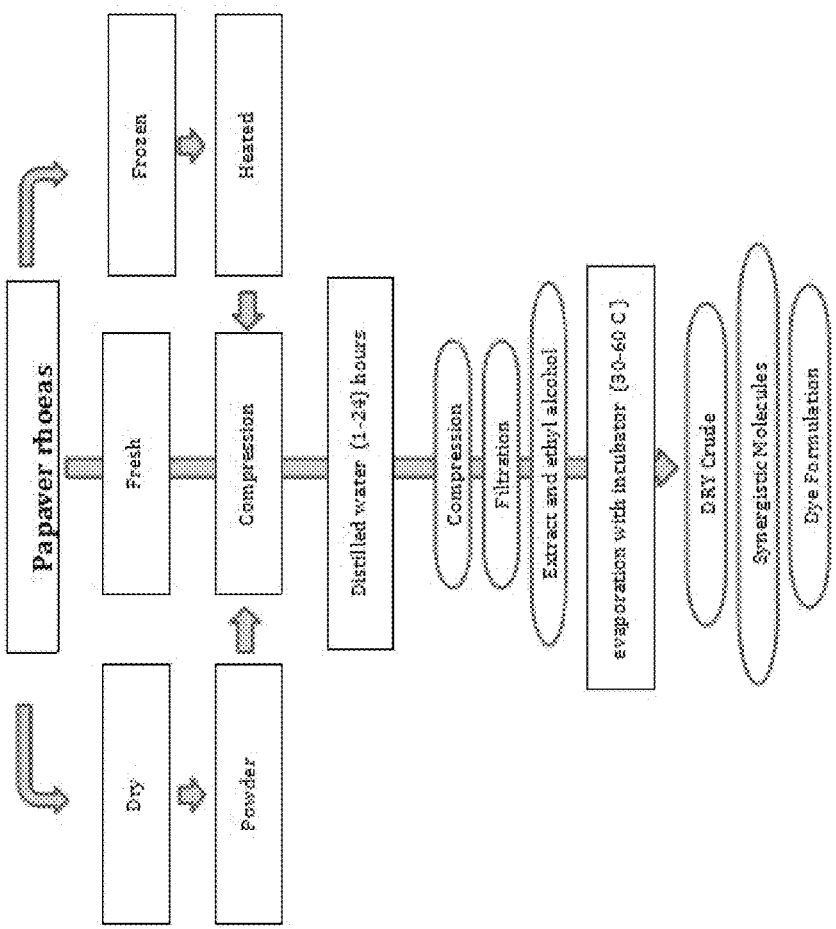
FIG. 3: Preparation techniques of the precursor of *Papaver rhoeas*

*Papaver rhoeas* is related to microscopic, molecular and atomic force microscopy investigations have been adjusted. (FIG. 1) for molecular analysis of the filtered extract solution is dried by incubation at half rate in hot ethanol. Dry sample is triturated three times and then subjected to one hour during the methanol bath. Again, the liquid fraction is evaporated in a night of 30-60 Celsius incubator and dried. 1 g of the resulting powder is dissolved in 100 cc of ethanol and adsorbed on a fiber plate. The pink plate with 1% ammonium solution specifically observed that bluish. This blue dye is dissolved in acetic acid. The liquid fraction was removed. And remaining dry powder is processed for analysis (FIG. 2,3).

The molecular analysis shows a characteristics of bioflavonoid and (FIG. 18) the Structural biochemical name; 5-hydroxy-7-methoxy-2-(4-methoxy-3-(((2R,3R,4S,5S,6R)-3.4.5-trihydroxy-6-((((2R,3R,4R,5R,6S)-3.4.5-trihydroxy-6-methyltetrahydro-2H-pyran-2-yl)oxy)methyl)tetrahydro-2H-pyran-2-yl)oxy)phenyl)-4H-chromen-4-one.

Figure 4:
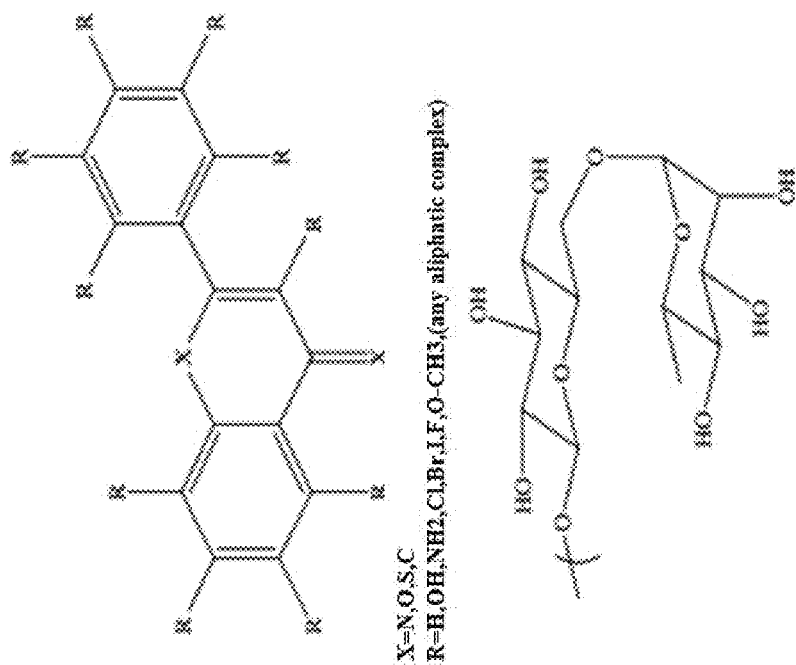
FIG. 4: The cis-trans chemical structure of *Papaver rhoeas* biyoflavonoid
Figure 5:
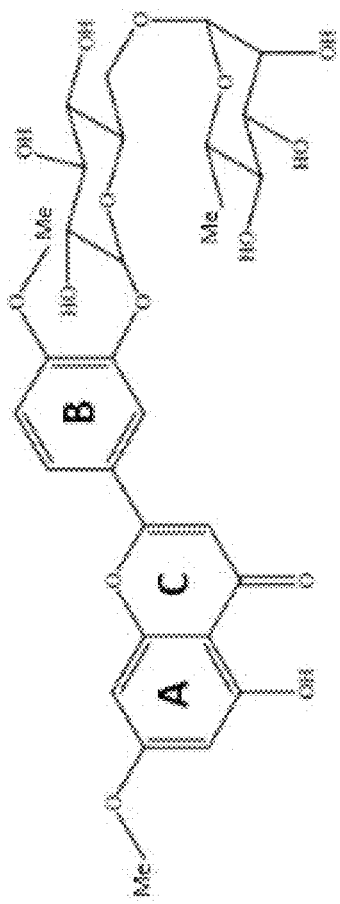
FIG. 5: The molecule's name and biochemical configuration

It has a characteristics biochemical configuration for bioflavonoids (FIG. 4,5)

*Papaver rhoeas* formula and Eosin (118) may be used as combination. The molecule and its derivatives synergistic bioflavonoids and the new molecule stains the tissue layers, membranes, muscle cells, detailing the intracytoplasmic and intranuclear structures as well as mucin and neuroglial fibers.

The stain formulation can be modified to utilized the uygun değer formula incorporated with the mordant, solvent, acid, oxidizing agent or oxidizing agent and preservatives (119)

Acid are generally used for adjusting the pH of the solution and can maintain a more durable stain formulation. and gives more selectively coloring the cells and prevents an excessive oxide. Therefore acid prevents the formation of precipitates. Automatic or manual staining methods can be chosen.

The stabilizing additive prevents the superfast oxidation and provides a longer shelf life basically through an optimisation. For this purpose, amylose, cyclodextrin, cryptands, cryptophycin, the Kavitand, a crown ether, Calixarene, valinomycin, cyclodextrin or Nigeria are used.

The liquid solvent is soluble in water join other antioxidants. For example, n-propyl, n-octyl and n-dodecyl, n-alkyl gallates gallates; can be reduced, such as sorbitol and mannitol are sugar; benzoates and hydroxybenzoates; sulphites and metabisulphites; citric acid, tartaric acid, lactic acid, erythorbic acid, ascorbic acid, uric acid, tannic acid, and basic salts (Mg2+, NH4 sup+, Na.sup.+K.sup.+ and Ca2+salts); EDTA and chloral hydrate is added One or more solvents can be used for *Papaver rhoeas* formula. Water, a lower alkanol such as ethanol, a polyol, and may be contained. Examples of polyols include glycerol, ethylene glycol, propylene glycol, polyethylene glycol and polypropylene glycol can be applied.

Formalin is a suitable fixative of tissue and cell samples. Paraffin tissue cassette are used for preparing and filled and embedded the samples and then are allowed to get frost. The fixed tissue with paraffin cut into thin sections with microtome cutter and placed on glass microscope slides. Then the preparations are placed in the oven to melt the excess paraffin and melted over the remaining wax. Dewaxing with xylene and toluene slide must be completely established.

The frozen tissue samples can be taken as sections of the staining process. Frozen tissue section for a short period, is kept in 10% formalin. Staining method, timing and sequencing may vary depending on the formulation method and other conditions. Opponents cytoplasmic staining on the Eosin Y, Orange 1 G, light green SF yellowish Bismarck Brown, fast green FCF, 0-6, EA25, EA36, EA50 and EA65 also used. (122)

The stain formula can be modified in the following dye formulations as in Gills, Anderson, Groot de Baker Bennett Bohmer, called Bosma Bullard Carazz of Coca Cola, from Debi, Delafield Duval, Ehrlich Friedlander, Gadsdo Gage, Galigh is, Garvey's, Graham, Mitchell Mayer Masson named Martinotti Mann Mallory says McLachlan iodine Lillie Lee Launoy Langeron Krutsay Kleinenberg Horneyold Haug Hamilton, Harris, Harris & Power's, Haugen's Molnar, Papamiltiades Pusey, Rawitz' Reddy, Sass', Schmorl, Sliders', Unna Watson's and Weigert and Wright and iron-mordant hematoxylin Anderson, Cretin, Faure, Goldman, Hansen, Heidenhain Janssen, Kefalas', including Krajina, the krutsay Manna, Lillie, Lillie and Earle, Masson, More & Bassal, Murray, Paquin and Goddard agaud Rozas', Seidel Thomas', Weigert and Yasvoyn or bismuth-mordant hematoxylin Roach & Smith is. Copper-mordanted hematoxylin Bensley, has named Cook and Faure. Held as of molybdenum-mordant hematoxylin year. Vanadium-mordanted hematoxylin Hedenham Smith, zirconium-mordant hematoxylin and McNulty & Smith (123) can be considered.

Other stains can be combined such as acridine dyes, anthraquinone dye, arylmethane dyes, azo dyes, diazonium dyes, dyes such as nitro dyes, can combine the (particularly methods of use of automatic) phthalocyanine dyes, quinine imine dyes, tetrazolium dyes, dyes and thiazole dyes, xanthene. Translation paint samples for histological staining, acetic acid, yellow acid, 1 black acid, 22 blue 93, acid fuchsin, acid green, acid, acid, 1 Green 5, Acid red, orange acid 10, acid red 4, acid red 26, acid, acid, acid red 29, acid red 44, acid red 51, acid red 66, acid red 73, acid red 87, acid red 91, acid red 92, acid red 94, 101 red 103, acid *rosea* the acid Rubin, acid violet 19, acid, acid, 1 yellow acid, 9 yellow acid, 23 yellow acid, 24 yellow acid, 36 yellow yellow 73, acid yellow S, acid yellow T, acridine, acriflavine, alcian blue, alcian yellow, alcohol-soluble eosin, alizarin, alizarin blue, alizarin blue 2RC, alizarin carmine, alizarin cyanine BBS alizarol cyanine R, alizarin red S, alizarin purpurin, alumina, amido black 10B, red amidonaphthol, amido schwarz, aniline blue WS, mauve, anthracene G azoeo're blue SWR, anthracene blue SWX, Auramine 0, azo-eosin, azocarm B, azocarm G, azoic diazo 5, azoic diazo 48, azophlox to, azov blue, deep blue, azure B, azure C, basic blue 8, the basic foundation, 9 blue foundation, 12 blue foundation, 15 blue foundation, 17 blue foundation, 20 blue foundation, 26 blue brown one, basically you Fusch, basic, 4 basic 5 red basic red 2 basic green, orange 14, basic, 5 green, basic essentials, 9 red violet 2, basic violet 4, basic violet 10, basic violet 14, basic essentials, 1 yellow yellow 2, Biebrich R, Bismarck brown Y, Brazil, Brazil, shiny Croc, brilliant crystal scarlet 6R scarlet Biebrich scarlet, calcium, red, carmine, carminic acid Carmoisine 6, Celestine blue B, china blue, chlorant fast red 5B, red, blue coelest the Chicago blue 4B, chrome violet CG, 2 chromotrop to, chromox until cyanine R, Congo Corinth, Congo red, cotton blue cotton, red, Crocker on red red 3D, Crocker's red Moon, sketch, crystal Ponceau 6R, crystal red, crystal violet, dahlia, diamond green B, direct blue 14, direct blue 58, Crocker direct direct red 28 red directly, 10 red, direct, 7 yellow directly, 81 red directly, 80 red, blue 4 durazol, blue 8G, yellowish, eosinol, eosin Y eosin eosin B, bluish eosin, eosin, durazol, Erie garnet B, eriochro to cyanine R, erythrosine B ethyl eosin, ethyl green, ethyl violet, Evan's blue, fast blue B, fast green FCF, fast red B, fast yellow, fast yellow extra fast yellow G, oily black HB, fluorescein, food green 3, galleon, gallamine blue gallocy's, gentian violet, yellow, lissamine fast yellow 1, INT, Kermes, kermesic acid, kemechtrot, Lac, laccaic acid, LAUTH the violet, light green, to root, 1 blue to root, quickly rub the BBL, helvetia blue, Hoffman's violet, hydrazine yellow, imperial red Helio lissamine green SF, Luxol fast blue, magenta, 0, magenta II, magenta II, magenta III, malachite green, Manchester brown, Martius yellow, lilac, mauve to, merbro my, Mercurochrome, methanyl yellow, methylene blue methylene azure B, methylene blue C, methylene blue, methylene green, blue, methyl, methyl green, methyl violet, methyl violet 2B, methyl violet 10B, yellow 3G milling, mordant blue 3, mordant blue 10, blue 14 mordant, mordant blue 23, blue 32 mordant, mordant 4 red natural mordant, 45 bluepurple, red-purple to 11, 3 25 red violet, purple to violet 39, naphthalene blue, black, naphthol blue, black, naphthol green B, naphthol yellow S, 1 natural black, natural red, natural red 3, natural scenic, 28 red natural, 25 red natural, 24 red natural, 16 red natural, 8 red, yellow 6, NBT, neutral red, get new fuchsin, Niagara blue 3B, blue night, Nile blue, Nile blue a, Nile blue sulfate, Nile red, nitro BT, nitro blue tetrazolium, nuclear fast red, oil red O, orange G, orcein, Pararosaniline Perkin violet, phloxine B, picric acid, Ponceau 2R, Ponceau 6R, Ponceau B, Ponceau de xylidine, Ponceau S, Ponta the sky blue 5B, primrose, *primula* to, purpurin, pyro B, G pyronin Y, rhodamine B, rosanil the pyro, OR, red R in red, Scharlach R, shellac, sirius red F3B, sirius red 4B safranin, Bengal, saffron rose Sirius blue above F3, solochro to cyanine R-soluble blue, solvent, 3 black solvent blue 38 solvent, 23 red a solvent, 24 red a solvent, 27 red a solvent, 45 red, yellow 94, spirit soluble eosin, Sudan III, Sudan IV Sudan black B, Sudan red BK, sulfur yellow S, Swiss blue, tartrazine, S thioflavin T, tion, blue, toluidine red toluene, tropaeol G, trypaflav the thioflavin, blue, Uranin trypan, Victoria blue 4R, Victoria blue B, Victoria blue R, Victoria green B, water-soluble eosin, woodsta red, xylidine Ponceau and eosin yellowish, and combinations thereof. (123-128)

In histology of the two most common metal as mordant as a synergistic molecule are aluminum and ferric iron, The mordants dyes forms a chelation with a covalent or coordination complex. Polyvalent metal ion of mordant and dye molecule creates coordination complexes. Chelate formation constitutes the "lake" which is defined as a dye-mordant multivalent complexes. This molecule has more than one attachment point, and the resulting in forming complexes are different in diversity and functionality.

Altering the pH level of formula demonstrates very abrupt and dramatic color change et. Sudden color change is explained by the change places with delocalized electrons and lower energy levels with the metal electrons. Metals have a relatively lower energy level in comparison with complex molecular structure, i.e. in the solution energy level suddenly drops by metal addition.

In the DNA structure of a base and is located behind a deoxyribose phosphate increased, thymine cytosine, guanine and adenine as form a helical structure in a complementary manner with mapping. Phosphate groups are fundamental for histological staining. Admixing Mordant to dye, the phosphate in DNA in will create a chelate formation.

The electrons necessary for forming a coordination bond assembly comes mordant dyes linked to a phosphate oxygen. DNA and proteins contain of hydroxyl and carboxyl groups and as does the nuclear chromatin, including protein components and DNA complexes. Therefore even after the stain is removed from DNA nuclear components still be visible.

Inadequately fixated tissues can not be optimally stained. Rapid processing techniques affect the staining quality. Applying 10% neutral buffered formalin for a few hours the fixation of proteins will be inadequate. Ethanol is a stabilizing agent and a dehydrating agent. Fixation with the formalin solution is sufficient for this purpose. When ethanol is used alone, brittle and distorted sections leave the artifacts of tissue.

Progressive staining method doesn't need to be differentiate in contrast to regressive method. The background staining besides the staining of the cell nuclei may also be desirable in varying degrees. Progressive solution shows a little or no background staining without mucin.

However, higher dye concentration (1.5-2.0 g/l) in acid addition provides a clear background staining as well. Regressive paint (especially 5 g/l dye concentration in the formula above) that appear to color stronger. After a regressive staining, differentiation provides a clear and clean nuclear morphologic appearance. Regressive formula may be preferred by a high-volume laboratuar and hospital.

Figure 6:
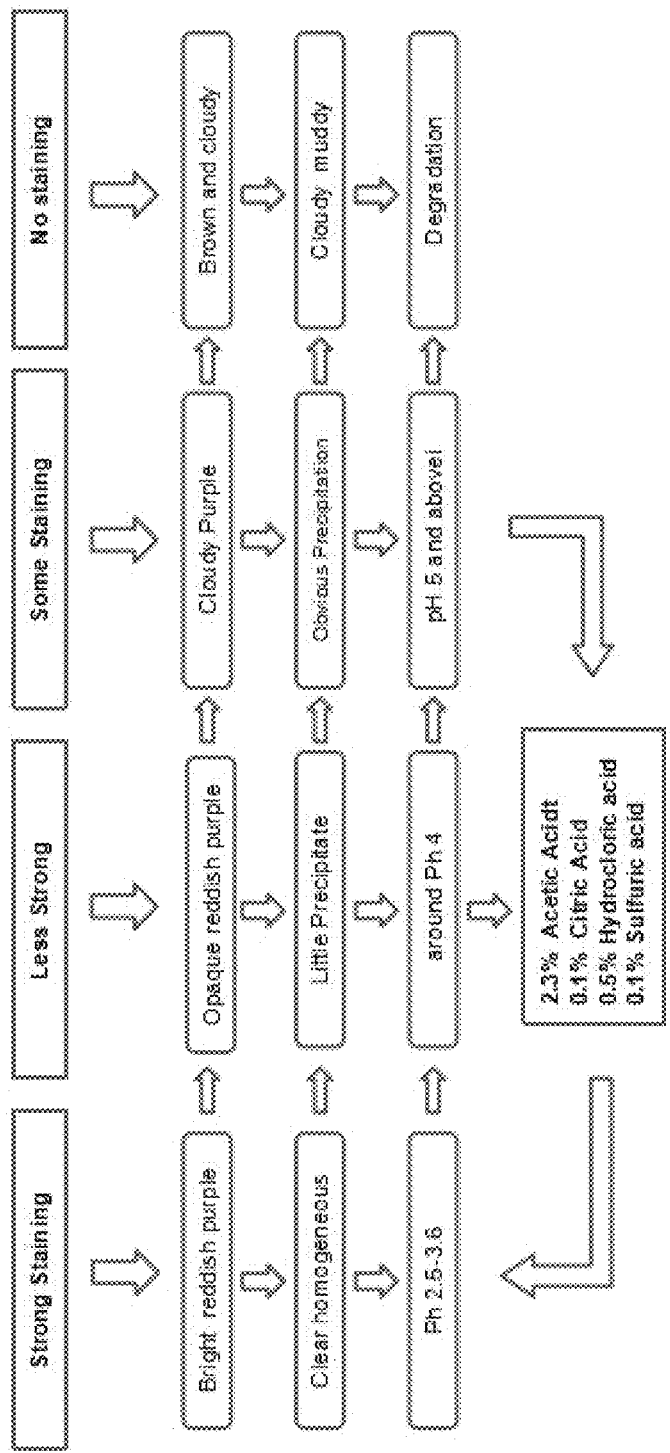
FIG. 6: *Papaver rhoeas* Formula Staining pattern

Aluminyum of ammonium and potassium, alone or aluminum with a solvent show a low pH levels, However if the buffering capacity is very limited and pH will increase eventually. However, adjusted to pH of acid dye of formula, the alkali solution into contact with the liquid in a short time will not affect the pH of the liquid. The lifetime of the dye solution, relates to mordant or dye back onto the carrying amount of the alkali liquid. In this way, the paint begins to decrease the activity. The first sign of the degradation is the change of the stain solution from red-bright purple color of red opaque cherry color. Activation with the addition of the acid dye into the dye solution fewer amounts involved. For this purpose, %2 5 percent acetic acid, 0.1% citric or 0.5% hydrochloric still tartaric acid, lactic acid, erythorbic acid, ascorbic acid, uric acid, tannic acid, should be determined with 1 liter of solution is on the required amount of pH control. Other acids which may also selected to control the pH. The pH of the solution should be around 2.5. However, modifications can be adjusted between pH 1-4 according to the formulas. (FIG. 6)

The addition of strong acid will dissolve the calcium storage in tissues and in stained tissue deposition of calcium is important to diagnose if (for example, breast cancer) may mislead the diagnosis. Therefore, very low pH values, which are strong acids should be avoided. Such as acetic and citric acid, should be expected to provide a formulation containing acid cleaner and significant core staining. Staining of nuclei with a progressive ideal formula containing a weak acid can be achieved in other words. In contrast acid which does not contain a formula to show better the background and will be less clear view to the kernel. Regressive addition of an acid in the formula will provide a contribution to staining but to provide clarity to come to the acidic pH of the dye solution increased the level again and will extend the life of the stain.

Figure 7:
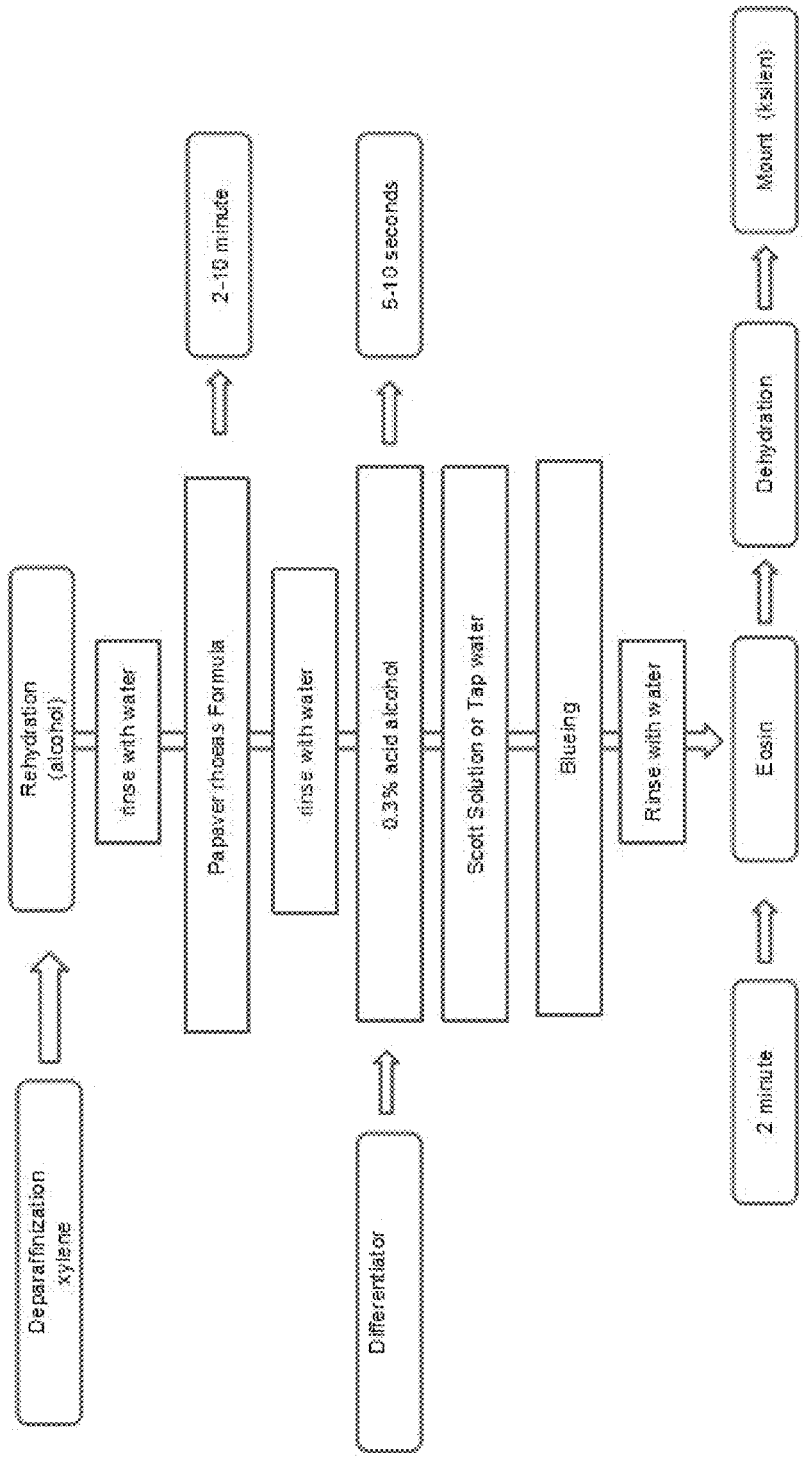
FIG. 7: Stages of *Papaver rhoeas* Formula Staining Method

The steps of staining protocols comprises 1. deparaffinization 2. Rehydration (using alcohol) 3. Rinse with water 4. *Papaver Rhoeas* formula Implementation 5. rinse with water to rinse 6. differentiation 7. rinse with water 8. blueing 9. rinse with water 10. rinse with alcohol 11. eosin 12. dehydration (using alcohol) 13. clearing with water (or xylene) (FIG. 7)

Staining time is applied as in other dyes and can be adjusted depending on the formulation ratios ranging from 30 minutes to one or two minutes (131 to 133). Very short incubation periods are result in incomplete and inconsistent staining. Fails to make adequate preparations can be corrected by agitations. Acid may clear out the artifacts on slides. However, this may decrease the effectiveness of the mordant dye complex. 15 seconds of agitation (shaking) with stain reduced to total staining period. If there is no agitation without agitation the duration should be longer.

It is sufficient to apply a 5-minute for staining. Length by adjusting the time the quality for progressive staining is adjusted. Ideally dyeing time is 5-10 minutes. Progressive painting is first started quickly and more independent for timing and later limits itself for the equilibrium point. For the regressive technique, 5-10 minutes is enough time. and excessive dye is removed by acid alcohol.

Differentiation with ethanol are applied for this purpose, varying concentrations of acid ethanol. The sample; 70% ethanol (standard acid alcohol) 0.5-% hydrochloric acid mixture used for 30-45 seconds. Dilution of strong acid dye is required to completely delete the clipboard. Herein may be used instead of ethanol, 70% distilled water. Water can dilute acid and differentiation may lead to the optimum staining. However, staining irregularities are encountered with the use of water instead of alcohol. n-iso-propanol can be chosen.

Figure 8:
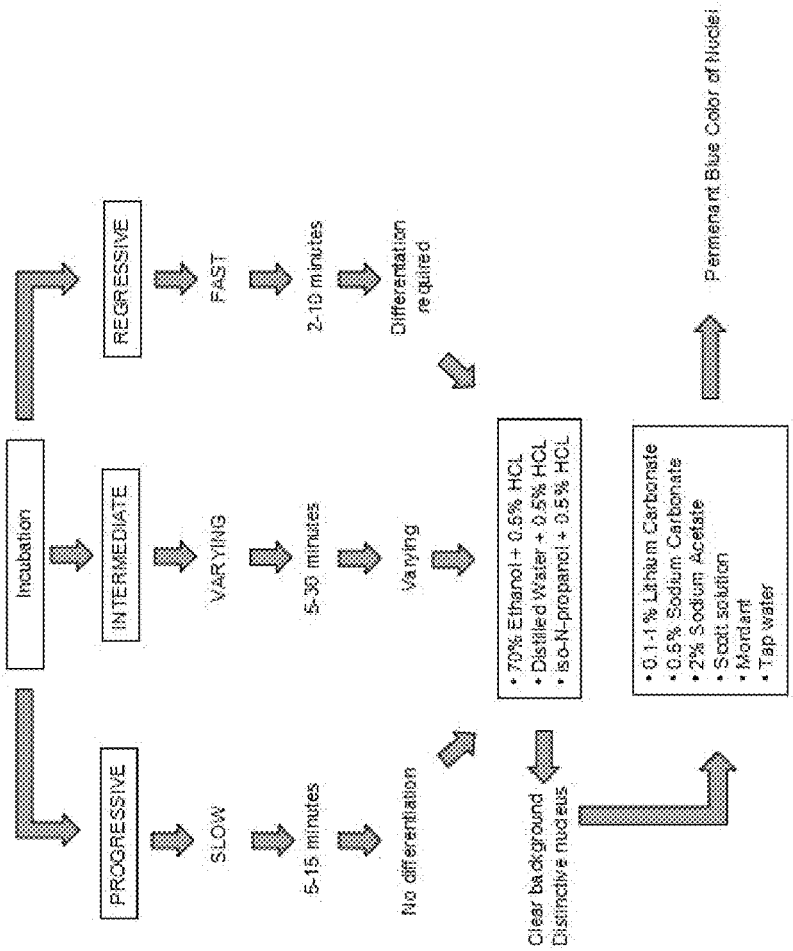
FIG. 8: Staining variation and differentiation

The initial color of the an acid medium on tissue slides is bright red-purple color. This is not a permanent color and should be converted to blue persistent color. The red phase of the color is leached out underneath mounted glass. The blue phase is resistant to solvents, insoluble and provided with water and mild solvents and permanent conversion is provided adjusting the pH. Tap water or other alkaline solutions provide the blueing. The water might be sufficient to turn the nuclei into blue as well as other alkali solutions such as 0.1-1% lithium carbonate solution, 0.5% sodium acetate, 2% sodium bicarbonate and Scott's tap water substitute. (FIG. 8)

Chlorine in the water can cause fading of paint colors on slides and may completely eliminate the staining and bleaching. In the case of the use of chlorinated water, washing by tap water must be eliminated secrets or non-chlorinated water should be used. High pH can inhibit the subsequent eosin staining if a strong alkali is used for blueing. Differentiation can be maintain with solvents to provided by pH control, fixatives, oxidizers and with other dyes.

The excessive stain can be reduced by the use of mordant. Compete for binding to tissue enters more mordant dyes contained in the solution and slowly separate the dye from the tissue. Complete removal is possible with this method over the stain preparations. Ripening will increase the efficiency of stain solution. Ripening; can be achieved by natural oxidation process is more reliable and durable. Oversize flask which is loosely closed with a cotton allowing entering the the air from top would be feasible Flask must be place in a warm, dark and airy place for slow oxidation is allowed.

Chemical oxidizing agents used in chemical ripening, providing faster and efficient maturation. Boiling speeds up the operation, after boiling sodium iodate, calcium hypochlorite, hydrogen peroxide, USP, potassium permanganate, potassium ferricyanide, sodium iodide, zinc oxide, can be used as the chemical oxidant besides potassium periodate and sodium hypochlorite.

When combined with an aluminum salt such as aluminum potassium sulfate, solution is pale color (immature) opaque transparent violet and when oxidized it turns to bright deep purple (ripened). They can also be combined with iron salts. These are very dark purple color is usually deep. Depending on the compound employed, oxalic acid, borax ferricyanide, potassium permanganate can be used as oxidant.

Main mordant for the staining solution of aluminum sulfate or potassium aluminum sulfate, ammonium aluminum sulfate, sodium aluminum sulfate. aluminum acetate and aluminum nitrate can. 5 grams per liter of paint powder to be used as the aqueous solvent, distilled water should be used. Mordant dye ratio approximately 10 times or may be a little less level. Excessive and continuous oxidation builds up the precipitate. This precipitate contains also contains mordant usually inactive derivatives of the resulting via oxidation. Stain formula is filtered periodically.

*Papaver Rhoeas* liquid formula which is obtained from the extract is dark red and handled with the different methods. Trituration of the product itself is suitable to be sold commercially (especially in terms of ease of transport) and prepared by the technician the hospitals and laboratories. The tested solutions are easy to transport as ready to use package or can be delivered to the appropriate hospital within dark containers.

By reacting with acetic acid nucleus chromatin core gives a more consistent and clear appearing nucleus image. Mordant aluminum paint formulation contains the acidic pH. (pH between −3.3 and −0.2.5). The effectiveness of the structures painted in length may be reduced if the dye containers moved during multiple washings with staining. Addition of new solution will strengthen the coating. There are less effective derivatives formed within solution after oxidation results and causes the formation of some precipitate. Liquid formula can store within barrel or container covered with a thin layer of oil to prevent the aerobic oxidation.

Figure 14:
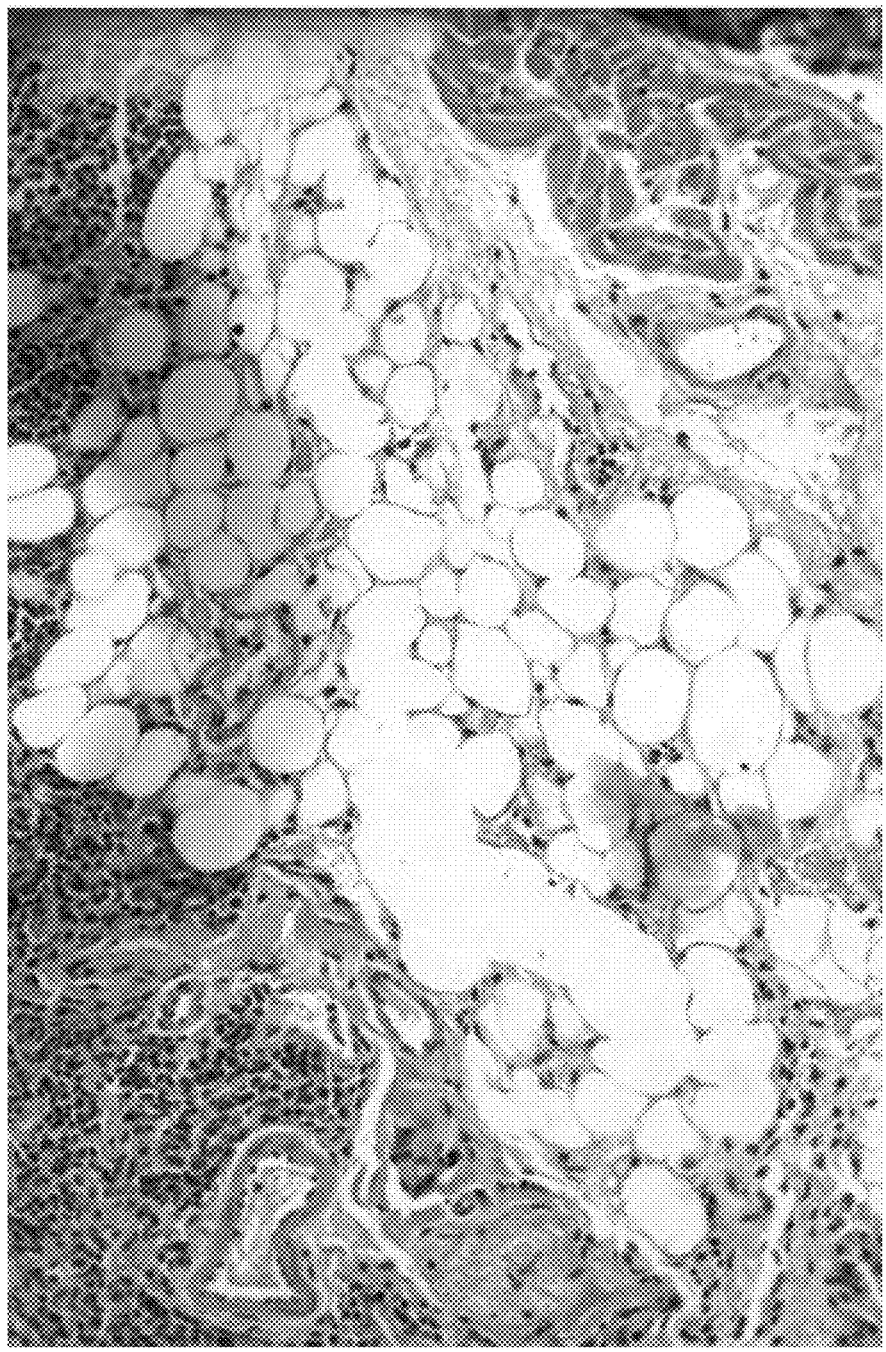
FIG. 14: *Papaver rhoeas* formula with Eosin in lung tissue revealing the nucleus and tissue details

Eosin Y, or other dyes can be used as counter stain the cytoplasm. General principles applicable here, but the result is a subjective assessment. A contrast dye is ideal not only make it look good with blue core components outside the nucleus should allow tissue to be clearly distinguished from each other as well (FIG. 14) must be able to distinguish from the collagen sample new muscle tissue. Eosin Y is normally soluble in 95% ethanol so if the lamella preparation CAs with closed once the alcohol is left on too long in my boyanmuşla will become colorless. If left too long in 95% ethanol, therefore, can be made with stained EO colorless tissue, it is less thank you 100% ethanol on the resolution of the Eon, but here, too, the paint is removed from the tissue. To avoid this problem, after eosinophilic preparations 7-10 times in rapid immersion should be washed with 95% ethanol subtraction or form. Eosin red color gives a suitable contrast to the blue core. Eosin Y is normally has a slightly yellow-orange color, but acetic acid, causing it to become redder.

The intensity of the red color, it is important to distinguish structures outside the nucleus. Inadequate stain causes faint staining on the other hand, too much stain off the nucleus makes it difficult to distinguish between the tissue structures. Eosin dye counter by combining collagen; pale pink color, muscle; dark pink, acidophilic cytoplasm; red, basophilic cytoplasm; purple, cores; dark purplish blue, red blood cells are stained red. Eosin must be applied to slides about 1 min. after staining *Papaver Rhoeas* formula.

More of eosin dye should be washed afterwards (129.130). Preferably, 50%, 75% and 95% concentration in a series of ethyl alcohol solution are selected for this purpose.

The termination of the staining process is an important criterion, but when is the best approach to visual evaluation of color intensity and contrast. Experience in preparation of standards and quality control of the staining results in improving as efficiency of the staining (134-138).

Figure 15:
FIG. 15: *Papaver rhoeas* Formula stains the structural details of fungi

*Papaver Rhoeas* formula is used for staining of non-human tissue biological samples. For instance yeast fungus in the sample from the yeast ball is stained with details (FIG. 15)

Figure 16:
FIG. 16: Proportional helical tubular structures within *Papaver rhoeas* Petal

Again it was observed that the petals of light and atomic force petals by examining the microscopy shows a cisternal structure arranged in a perfect alignment filled with the liquid produced by the an excellent proportional helical tubes. (FIG. 16,17)

EXAMPLES

1. Example 1. Preparation of precursor: frozen, fresh or dried petals *Papaver rhoeas* (petals) employed in the preparation of dye extracted (FIG. 9) The leaves are fragmented. Distilled water and then allowed to stand overnight with the addition of this procedure is then compressed to extract liquid dye precursor is obtained. First Dyes purple, red, purplish red, reddish purple and reddish blue. After filtration the solution is such as to provide 1/10 ratio formalin, ethanol, methanol, a solvent is incorporated as the other ether and dried out with heat in an incubator at 30 to 60 Celsius degrees. The dried crude material was treated again with methanol and the precipitate is separated. This precipitate is used to prepare powder crude. This precipitate is added into cold or boiling ethyl alcohol (1 g paint/100 ethyl alcohol) and dissolved. This liquid mixture (cold or boiling temperature) is added to 1000 ml of deionized water.

2. Example 2: For Molecular analysis, the extract solution was filtered and treated with ethanol and dried out within incubator. Dry sample pulverized and then passed through a methanol bath three times during. and placed into the incubator overnight at 30 to 60 Celsius degree and the liquid fraction is evaporated. 1 g of the resulting powder is dissolved in 100 cc of ethanol and absorbed onto the fibers on the plate. The blueing of the pink plates with 1% ammonia solution is observed. This blue dye is dissolved in acetic acid. The liquid fraction was removed. And to the remaining dry powder analysis.

Figure 10:
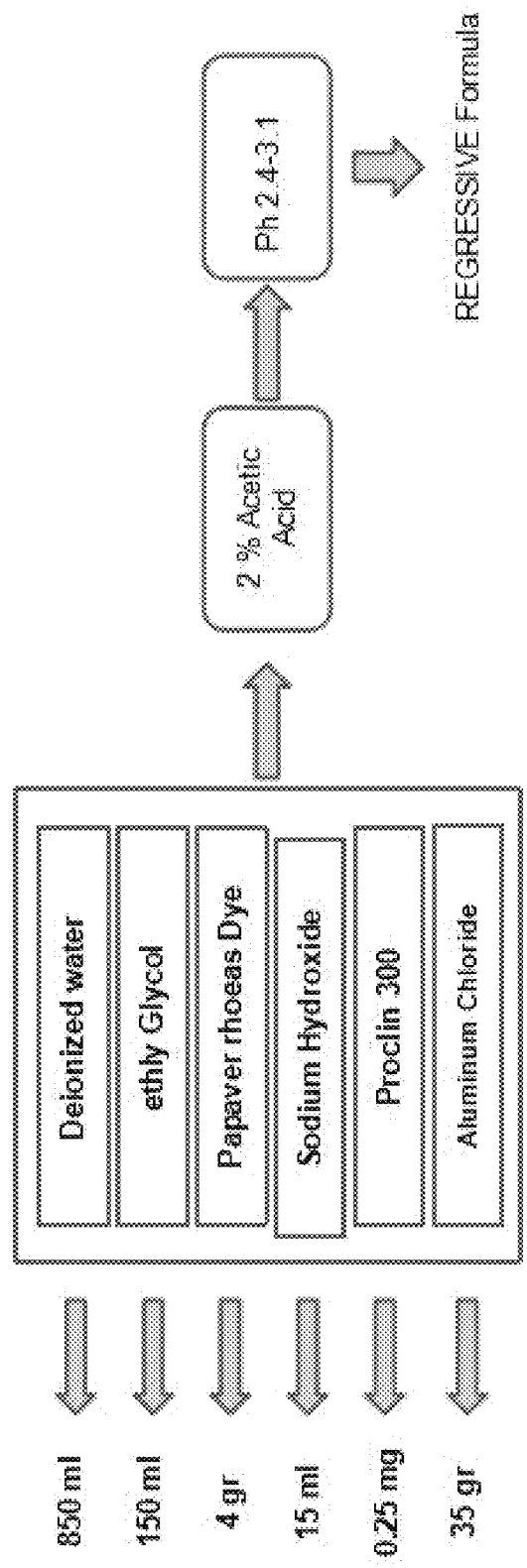
FIG. 10: The example for *Papaver rhoeas* formula preparation

3. EXAMPLE 3; The chemical oxidizing agent used in the composition of this new molecule partially or completely. Derivatives of the molecule will form as a result of oxidation. However, less active complexes may also be formed The molar balance of the oxidant and molecule is between 4:1 and 1:1. Dye within solvent has multiple mordant. (Aluminum. Iron bismuth mordant, copper, molybdenum, chrome and vanadium, and zirconium) (120, 121) The molar ratio of molecular and mordant is 2:1 and 1:100, this ratio differs depending on formulations, for instance it is changed between 1:20 and 1:5. Formula may also contain an acid such as acetic acid. Final mordant dye and solvent solution (e.g AlCl3 80%. 10-50 g/liter) has an acidic pH, Adding the the acid to formula regulates the specificity of nuclear staining and increased the shelf life. Bluing highlights the shape of cell nucleus. The addition of acetic to dye formula turn the color into bright brownish purple. (FIG. 10)

4. EXAMPLE 4 Although the ideal pH for formulation is 2.5 it varies from 1 to 4. In some particular embodiments, the oxidant is sodium iodate in a composition, aluminum sulfate as a mordant, aluminium chloride antioxidants as β-cyclodextrin, by 60 to 90% water as a solvent and can be used at the rate of 10 to 40% ethylene glycol mixture. Such as n-propyl gallate, hydroquinone, and one or more water-soluble antioxidants can be used.

5. Example 5: Coloring is established as in progressive or regressive fashion. Biological samples are supported by a microscope slide. The method also can be used for cytology samples mounted on a microscope slides. Counterstaining, Eosin is chosen 6. EXAMPLE 6: Stabilizers prevent the over oxidation, evaporation and eventually precipitation. Stain formulation is prepared with the amount of solvent and dye/solvent ratio is set at 1-20 grams to 1 liter. Minimum 1 gram dye for per liter for progressive solutions, and regressive paint contains at least 5 grams for per liter of solvent. When the amount of mordant remains constant, less concentrated dye in the solution reveals more selective staining of the cell nucleus. For instance 5 mL of 10% solution of a dye and and increasing amounts to over 10% alcoholic dye solution is added to reach the optimum selectivity.

7. EXAMPLE 7: If the concentration is lower and mordant dyes/dye ratio of the dye in the solution is high, remains in the solution and a small amount of dye adhere to tissue. Adding an acid such as 0.1% or 2% acetic acid, citric acid, extend the shelf life.

Figure 9:
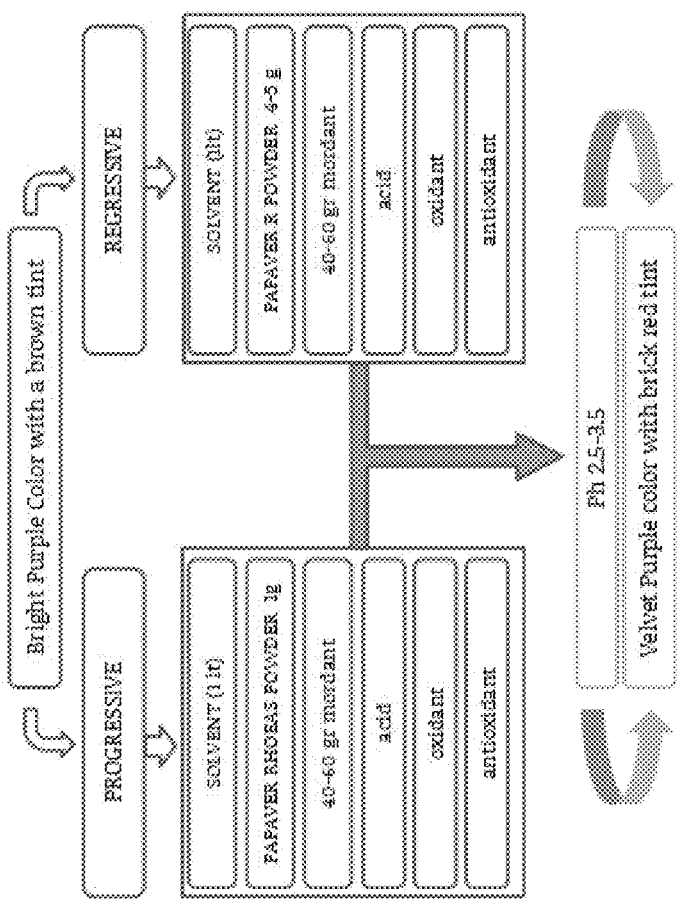
FIG. 9: *Papaver rhoeas* cells and tissues stain types based on staining pattern

8. EXAMPLE 8: Very low pH level solutions is important for the diagnosis since tissue calcifications also may dissolves. Therefore, diagnosis can lead to errors and omissions with solution with strong acids. Increasing concentrations of 0.2 ml glacial acetic acid, or can be tested by adding 0.1 ml HCl acid. 5 g of dye and 50 g of mordant (Aluminum sulfate) acidic by use regressive staining formula is obtained (ratio of 1/10s), 1 g dye and 50 g of mordant (Aluminum sulfate) progressive acid with the use of staining formula is obtained. (ratio 1/50 is) (FIG. 9)

9. EXAMPLE 9 1000 ml of deionized water boiling point is placed in a large flask. This includes 50 g of ammonium sulfate is added and the mixture is allowed to cool. 4 g of dry powder is placed within a flask stirred with 0.4 g of sodium iodide are dissolved in 50 ml of cold water. 100 cc of ethylene glycol was added and mixed with it and 10 cc of acetic acid is added. (pH unit to be between 2.7 and 3.1). Stock solutions are mixed with each other. The paint is ready for use. Application time for painting should be optimized by trial.

10. EXAMPLE 10: Modifications are also possible. Acid addition of 100 g of acid-free regressive wherein 5 g of dye mordant dye of formula with. Here ratios of 1/20 is. (5 g dye+100 g of aluminum sulfate). 1-2 grams for progressive per liter, and 5-6 g of regressive and Intermediate formula contains 3-4 grams of stain. The preparation of dye and application should be well understood by the technician. Changing the content of the dye can adjust the quality of the resulting dye.

1. Example 11: The produced powder is brick reddish purple brown and soluble with ethanol and less soluble with water (100 cc of water, but 1 g of dye solving 100 g ethyl alcohol 35-50 g solves removing paint.) The glycerin can be incorporated as an antioxidant and prevents the excessive oxidation formula and also prevents the development of fungi. Any antimicrobial agent such as Proclin 300® sodium azide, Proclin 150®, an antimicrobial agent such Proclin Proclin 200® and 950® is added. to inhibit microbial growth within the pH unit of 2.0-5. (For instance) To the solution in an amount of about 0.04% Proclin 300® (Sigma Aldrich, St Louis, Mo.) (FIG. 10)

The invention claimed is:

1. A tissue-cell-nucleus staining formulation comprising
(i) a tissue-cell-nucleus staining molecule having the structure of

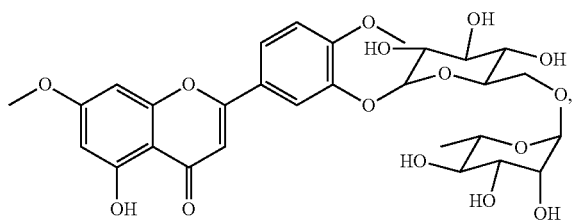 [SMILES: COc1cc(O)c2c(=O)cc(-c3ccc(OC)c(OC4OC(COC5OC(C)C(O)C(O)C5O)C(O)C(O)C4O)c3)oc2c1]

(ii) a solvent,
(iii) a mordant, and
(iv) an oxidant;
wherein a molar ratio of the tissue-cell-nucleus staining molecule and the mordant is 2:1 to 1:100 and pH of the formulation is from 1 to 4.

2. The tissue-cell-nucleus staining formulation of claim 1, wherein the mordant is at least one of metals selected from the group consisting of iron, bismuth, copper, molybdenum, vanadium, and zirconium.

3. The tissue-cell-nucleus staining formulation of claim 1, wherein the mordant is selected from the group consisting of Aluminum sulfate, ammonium aluminum sulfate, aluminum acetate, aluminum nitrate, and potassium aluminum sulfate.

4. The tissue-cell-nucleus staining formulation of claim 1, wherein the oxidant is selected from the group consisting of sodium iodate, calcium hypochlorite (bleach), hydrogen peroxide, potassium permanganate, potassium ferricyanide, sodium iodide, zinc oxide, potassium periodate and sodium hypochlorite.

5. The tissue-cell-nucleus staining formulation of claim 1, further comprising one or more antioxidants and n-propyl gallate.

6. The tissue-cell-nucleus staining formulation of claim 1, further comprising a water-soluble anti-oxidant additive.

7. The tissue-cell-nucleus staining formulation of claim 1, wherein the solvent is selected from the group consisting of ethanol, water, methanol, ethylene glycol, propylene glycol, and formaldehyde.

8. The tissue-cell-nucleus staining formulation of claim 1, further comprising an antimicrobial agent selected from the group consisting of Proclin 300®, sodium azide, Proclin 150®, Proclin 200® and 950® Proclin.

9. The tissue-cell-nucleus staining formulation of claim 1, further comprising at least one dye selected from the group consisting of an acridine dye, an anthraquinone dye, an arylmethane dye, an azo dye, a diazonium dye, a nitro dye, a phthalocyanine dye, a quinone imine dye, a tetrazolium dye, a thiazole dye, and an xanthene dye.

10. The tissue-cell-nucleus staining formulation of claim 1, wherein the molar ratio of the tissue-cell-nucleus staining molecule and the mordant is 1:20 to 1:5 and the pH of the formulation is 2.5.

11. A method of staining a tissue or cell or nucleus, wherein the tissue or cell or nucleus is stained with the formulation of claim 1.

12. The method of claim 11, wherein a tumor biopsy, a fine needle biopsy sample, a smear, wash, surgery, post-operative surgery and other invasive and non-invasive samples and samples of a biological material are assessed and diagnosed with the tissue-cell-nucleus staining formulation.

13. The method of claim 11, wherein a biological sample is a human, an animal, a plant and microbiological.

14. The method of claim 11, wherein a biological sample origin is a prokaryotic, archaeal, eukaryotic, mammalian origin or a primate origin.

15. The method of claim 11, wherein the formulation is applied in a plurality of vivo or in a plurality of vitro biological samples.

16. The method of claim 11, wherein a different counter-stain selected from the group consisting of Eosin Y, orange G, light green SF yellowish brown Bismarck, fast green FCF, O-6, EA25, EA36, EA50 and EA65 is used in combination with the formulation of claim 1.

17. A tissue-cell-nucleus staining formulation comprising
   (i) a tissue-cell-nucleus staining molecule having the structure of

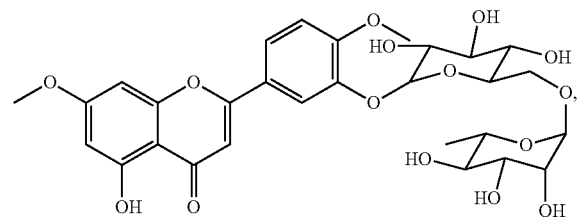 [SMILES: COc1cc(O)c2c(=O)cc(-c3ccc(OC)c(OC4OC(COC5OC(C)C(O)C(O)C5O)C(O)C(O)C4O)c3)oc2c1]

(ii) a mordant;
   wherein a molar ratio of the tissue-cell-nucleus staining molecule and the mordant is 2:1 to 1:100 and a pH of the formulation is from 1 to 4.

* * * * *